US011697119B2

(12) United States Patent
Davidowitz et al.

(10) Patent No.: US 11,697,119 B2
(45) **Date of Patent: *Jul. 11, 2023**

(54) STORAGE SYSTEM FOR BIOLOGICAL SAMPLES AND THE LIKE

(71) Applicant: BioTillion, LLC, Skillman, NJ (US)

(72) Inventors: Hananel Davidowitz, Princeton, NJ (US); Theodore N. Altman, East Windsor, NJ (US); Ke Wang, Flemington, NJ (US); Ron Or, Moshav Bney Atarot (IL); Zhengyan Zhai, Doylestown, PA (US); Jeremy Basch, Middlesex, NJ (US)

(73) Assignee: BioTillion, LLC, Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/501,437

(22) Filed: Oct. 14, 2021

(65) Prior Publication Data

US 2022/0072533 A1 Mar. 10, 2022

Related U.S. Application Data

(63) Continuation of application No. 16/056,696, filed on Aug. 7, 2018, now Pat. No. 11,148,143.

(60) Provisional application No. 62/542,392, filed on Aug. 8, 2017.

(51) Int. Cl.

| | |
|---|---|
| ***B01L 99/00*** | (2010.01) |
| ***B01L 3/00*** | (2006.01) |
| ***A61B 10/00*** | (2006.01) |
| ***G01N 35/00*** | (2006.01) |
| ***B65G 1/137*** | (2006.01) |
| *B01L 7/00* | (2006.01) |

(52) U.S. Cl.

CPC ........ *B01L 3/5085* (2013.01); *A61B 10/0096* (2013.01); *B01L 3/545* (2013.01); *B65G 1/1371* (2013.01); *G01N 35/00732* (2013.01); *B01L 7/50* (2013.01); *B01L 2300/022* (2013.01); *B01L 2300/023* (2013.01); *B65G 2203/046* (2013.01); *G01N 2035/00445* (2013.01); *G01N 2035/00772* (2013.01); *G01N 2035/00801* (2013.01)

(58) Field of Classification Search

CPC .......... B01L 3/5085; B01L 3/545; B01L 9/52; B01L 2300/021

USPC .................................................. 422/566, 565

See application file for complete search history.

(56) References Cited

U.S. PATENT DOCUMENTS

| | | | | |
|---|---|---|---|---|
| 8,346,382 | B2 | 1/2013 | Davidowitz et al. | |
| 8,378,827 | B2 | 2/2013 | Davidowitz et al. | |
| 8,852,536 | B2 | 10/2014 | Davidowitz et al. | |
| 8,872,627 | B2 | 10/2014 | Davidowitz | |
| 9,431,692 | B2 | 8/2016 | Davidowitz et al. | |
| 2009/0322486 | A1 * | 12/2009 | Gerstel ................ | B65G 1/1371 340/10.1 |
| 2014/0230472 | A1 * | 8/2014 | Coradetti ............. | A01N 1/0268 62/125 |
| 2014/0352456 | A1 | 12/2014 | Davidowitz | |

* cited by examiner

*Primary Examiner* — Natalia Levkovich

(74) *Attorney, Agent, or Firm* — Mendelsohn Dunleavy, P.C.; Steve Mendelsohn

(57) ABSTRACT

A storage system having racks and an outer container that receives the racks, each rack receiving a plurality of sample boxes, each box having a wireless ID tag. In certain embodiments, the storage system has reader electronics external to and distinct from the racks and that directly read the wireless ID tag of each box in at least one rack without relying on any reader electronics of any rack. In other embodiments, each rack has a set of rack reader electronics that read the wireless ID tag of each box in at least one rack, and the storage system has at least one removable reader access device removably connectable to the set of rack reader electronics of a rack in order to transmit the ID number of the wireless ID tag of each box in the rack outside of the outer container.

16 Claims, 30 Drawing Sheets

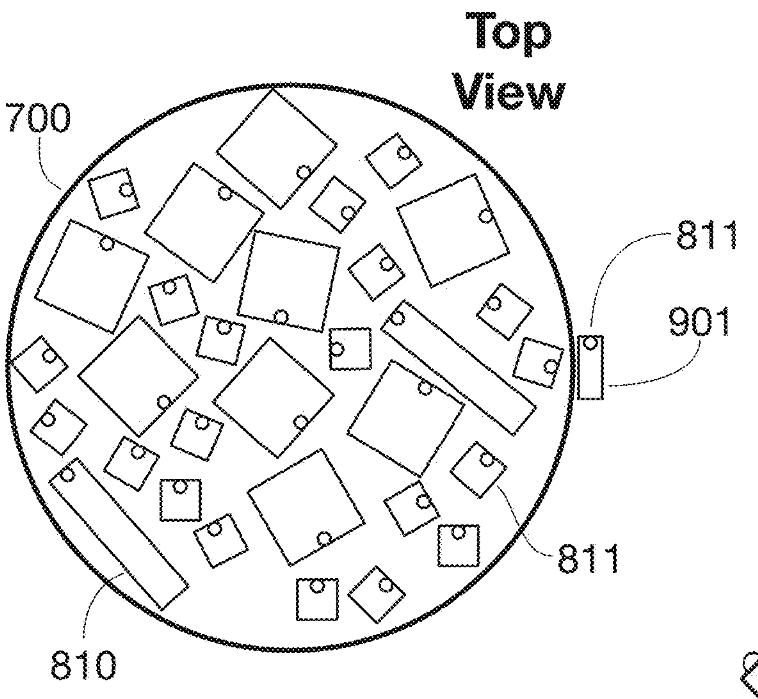
FIG. 9A
FIG. 9B
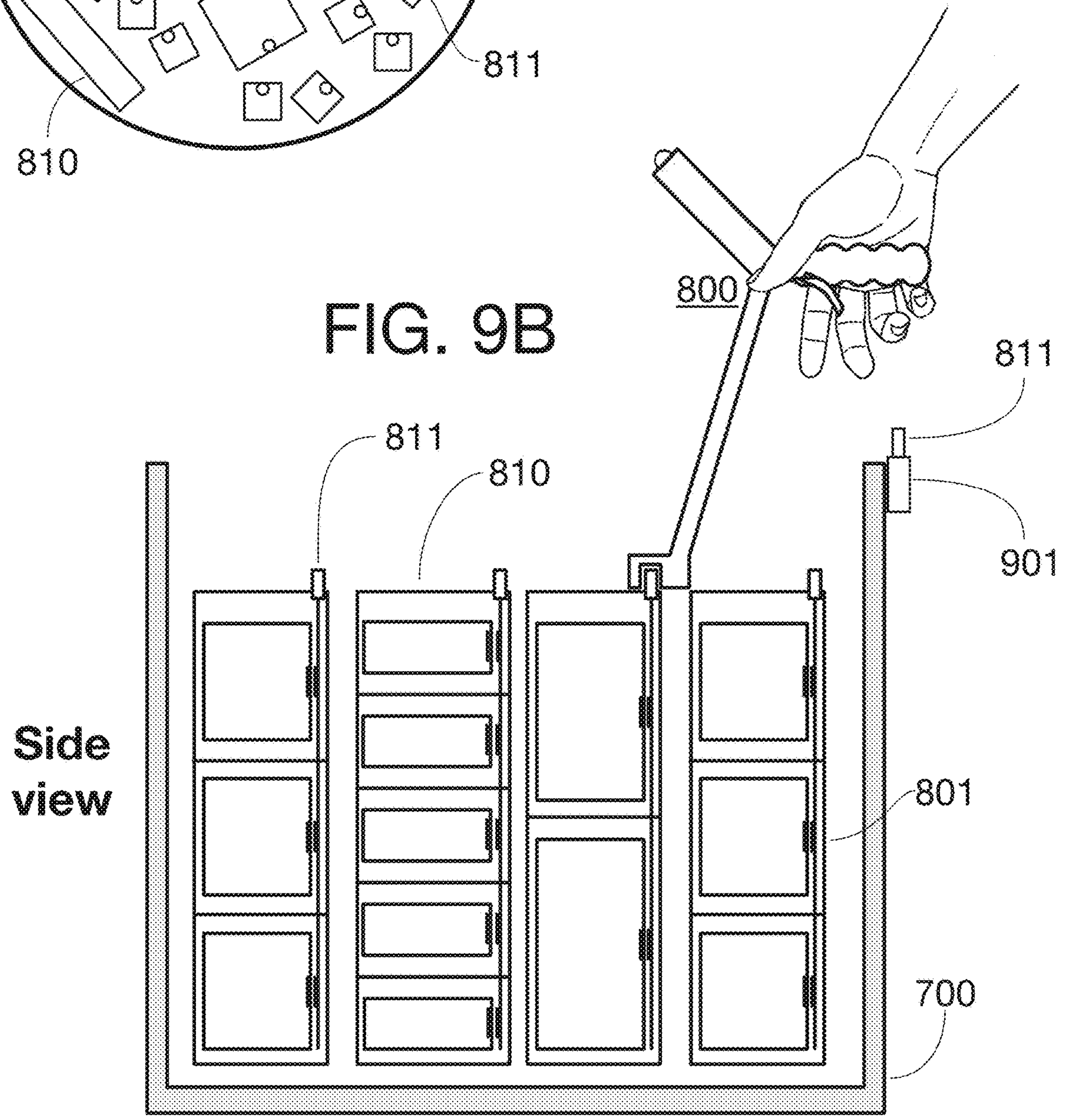

1510, 1514

2401

STORAGE SYSTEM FOR BIOLOGICAL SAMPLES AND THE LIKE

CROSS-REFERENCE TO RELATED APPLICATIONS

This application is a continuation of U.S. patent application Ser. No. 16/056,696, which claims the benefit of the filing date of U.S. provisional application No. 62/542,392, filed on Aug. 8, 2017, the teachings of both of which are incorporated herein by reference in their entirety.

The subject matter of this application is related to the subject matter in U.S. Pat. Nos. 8,346,382, 8,852,536, 8,378,827, 8,872,627, and 9,431,692 and U.S. patent application Ser. Nos. 14/462,618 and 14/184,815 (collectively, "cited patent matters"), the teachings of all of which are incorporated herein by reference.

STATEMENT REGARDING FEDERALLY SPONSORED RESEARCH OR DEVELOPMENT

The Government of the United States of America has rights in this invention pursuant to Cooperative Agreement No. OD018230 awarded by the U.S. National Institutes of Health.

BACKGROUND

Field of the Invention

The present invention relates to systems for storing and retrieving samples and, more particularly but not exclusively, to cold-storage systems for biological samples.

Description of the Related Art

This section introduces aspects that may help facilitate a better understanding of the invention. Accordingly, the statements of this section are to be read in this light and are not to be understood as admissions about what is prior art or what is not prior art.

Conventional systems used to track boxes of biological samples in ultra-low temperature freezers are complex. A recent implementation for a freezer designed to store 600 boxes of samples (the ColdSIGHT™ freezer by BioTillion) uses 235 printed circuit (PC) boards of 8 different types and 11 cables. The ColdSIGHT™ freezer has special racks and shelves, each of which contains electronics, where data and power are wirelessly transferred between the racks and shelves.

BRIEF DESCRIPTION OF THE DRAWINGS

Embodiments of the invention will become more fully apparent from the following detailed description, the appended claims, and the accompanying drawings in which like reference numerals identify similar or identical elements.

FIGS. 9A and 9B show top and side views, respectively, for a freezer;

DETAILED DESCRIPTION

Detailed illustrative embodiments of the present invention are disclosed herein. However, specific structural and functional details disclosed herein are merely representative for purposes of describing example embodiments of the present invention. The present invention may be embodied in many alternate forms and should not be construed as limited to only the embodiments set forth herein. Further, the terminology used herein is for the purpose of describing particular embodiments only and is not intended to be limiting of example embodiments of the invention.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

A typical hierarchy of a sample bank (or repository) is one or more freezers, each freezer containing one or more shelves, each shelf containing one or more box racks, each box rack containing one or more boxes, each box containing one or more samples. Thus, the address of a particular sample can be summarized as "freezer ID: shelf ID: rack ID: box ID: sample location ID," where each ID is a number that uniquely identifies the corresponding item among other items of that same type.

In prior art, such as the prior art described in the cited patent matters, RFID-tagged boxes are inserted into racks that have electronics that a) read the box tags and b) communicate with the corresponding shelf to receive commands and relay box data to the rest of the system. The shelf and racks have built-in electronics that are proprietary to the system. Data and power are transferred wirelessly between the shelf and each rack.

In one implementation, a cold-storage system for biological samples comparable to the BioTillion ColdSIGHT™ freezer employs only 31 PC boards of two types and 6 cables. In addition, no special racks are required and no wireless interactions other than the box RFID reading itself are needed. Here disclosed is a new method for tracking sample boxes in an ultra-low temperature freezer. The principles presented here can be implemented in any suitable storage systems, including (without limitation) freezers and refrigerators that are not maintained at ultra-low temperatures, such as blood bag refrigerators, and even non-refrigerated storage systems, such as wax tissue blocks (FFPE samples).

Figure 1A:
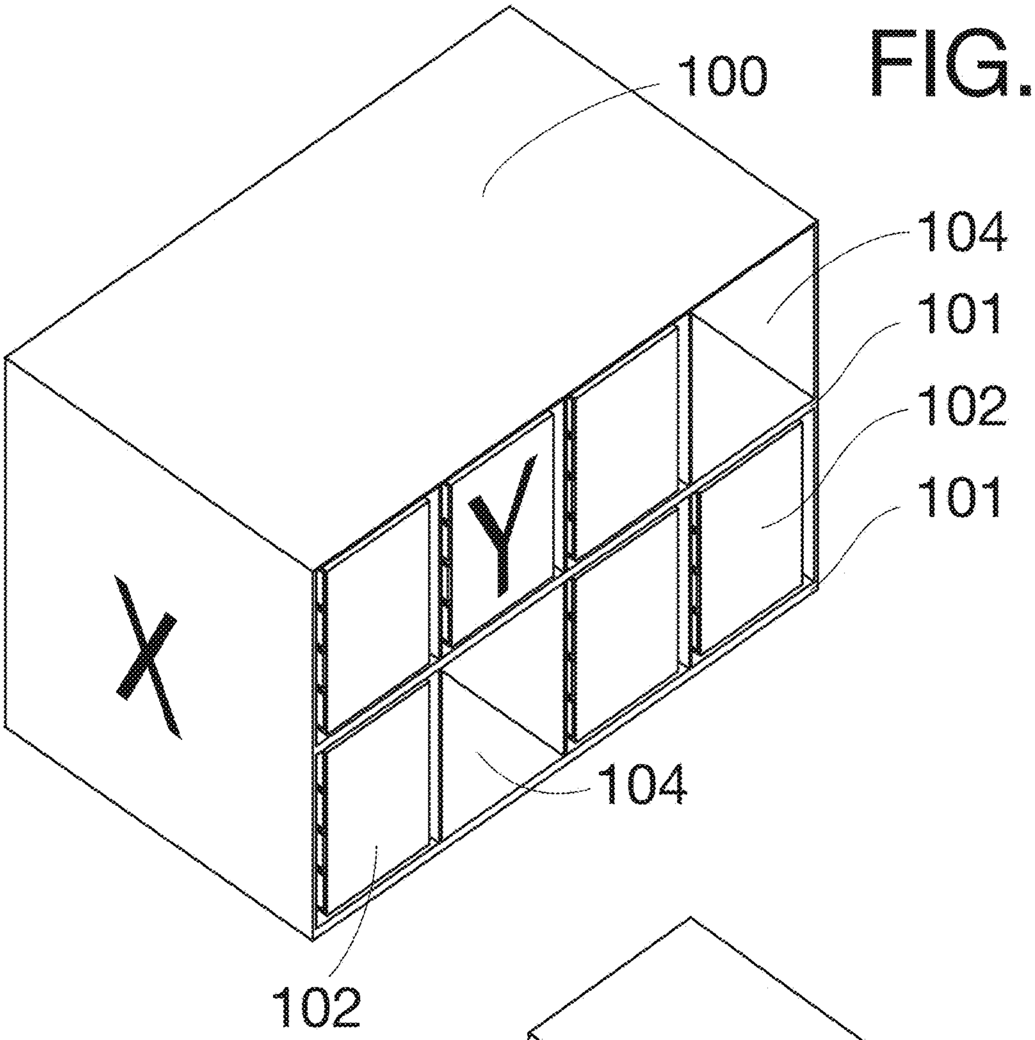
FIG. 1A shows a simplified 3D view of an ultra-low temperature freezer.

FIG. 1A shows a simplified 3D view of an ultra-low temperature freezer 100. In this simple example, the freezer has two shelves 101, each of which can hold four racks 102. For example, racks 102 are shown occupying three of the four possible rack positions 104 on each of the top shelf 101 and the bottom shelf 101.

Figure 1B:
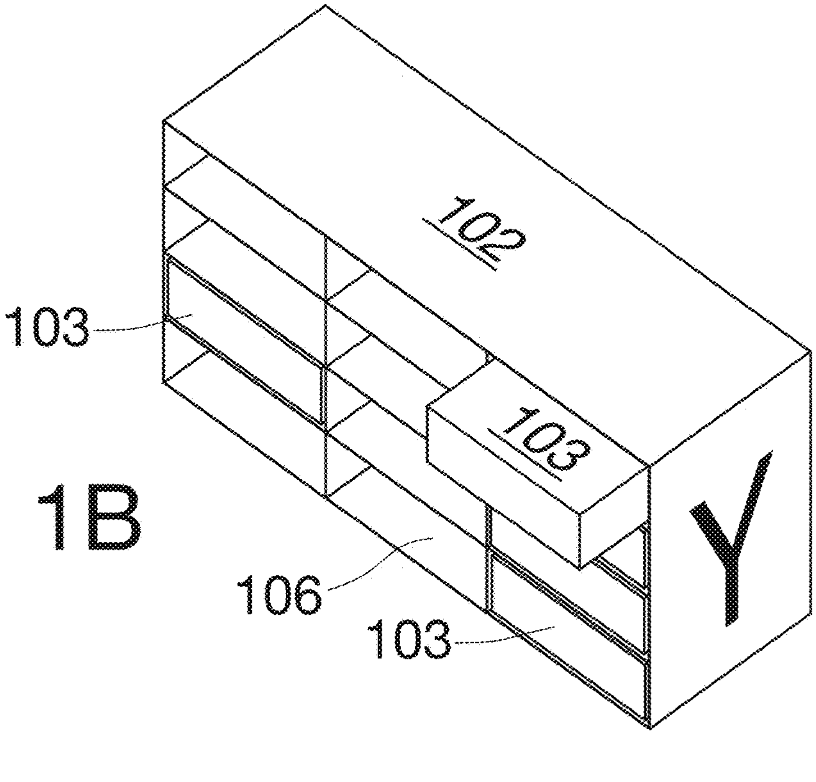
FIG. 1B shows a simplified 3D view of a rack for the freezer of FIG. 1B.

FIG. 1B shows a rack 102 with 12 box locations 106, where the rack 102 is partially filled with five out of the maximum of 12 boxes 103. The top right box 103 is shown partially removed for clarity. A unique box RFID tag (not shown in FIG. 1B) is located on the back face of each box 103.

Freezer configurations can vary. A typical upright freezer can have six shelves 101, each shelf holding five racks 102 with each rack holding 20 boxes 103 for a total of 600 boxes. The upright freezers and parts thereof depicted in FIGS. 1-4 are more modest, primarily so that the figures will not be overly complex. In FIGS. 1-4, the freezers have two shelves 101, each shelf holding up to four racks 102, each rack holding up to 12 boxes 103 for a maximum total of 96 boxes. The system described herein can be scaled so that it can be adapted to many different freezer configurations.

Figure 2A:
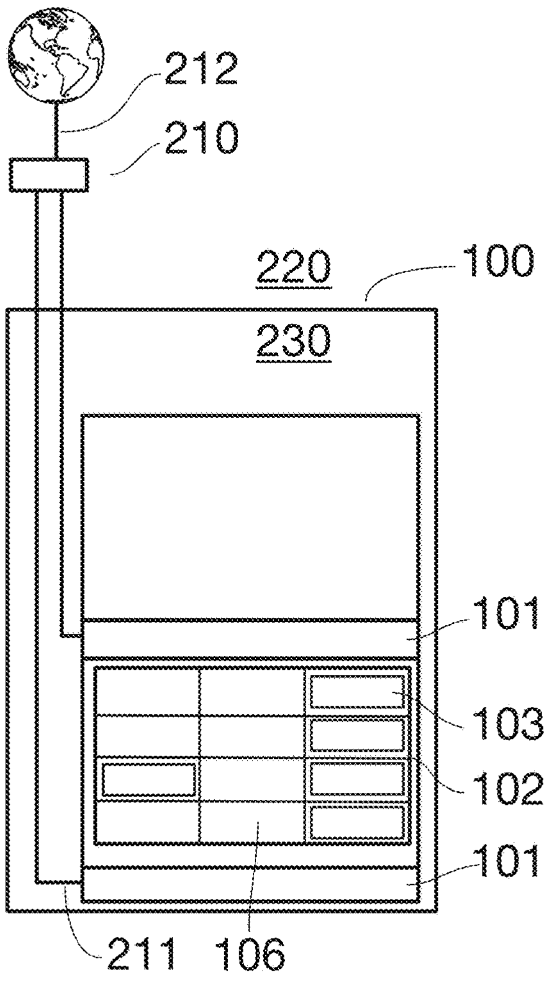
FIGS. 2A and 2B show X-ray side views of two freezers.

FIG. 2A shows an X-ray side view of freezer 100 as would be seen when looking through side X in FIG. 1. A system controller 210 communicates with and supplies power to the shelves 101 via wired electrical connections 211. The system controller 210 will usually, but not necessarily, be located in the ambient, room temperature environment 220 outside of the cold interior 230 of the freezer. The controller 210 can initiate read requests performed by the shelves 101 of the box RFID tags on the boxes 103 placed in any given rack 102. Box identification data is transmitted from each shelf 101 to the controller 210 via the electrical connections 211. The controller 210 can also control indicators such as LEDs on the shelves, read temperatures throughout the freezer, and so on, as will be explained later.

The system controller 210 sends data to and receives commands from an external sample management system (not shown) through a wired or wireless connection 212. The sample management system is a processor-based system, e.g., a desktop or laptop computer that can be either local to the freezer or in a remote location. It is typically located outside of the freezer and configured to manage the operations of one or more freezers and maintain a database of the samples stored in those freezers. The connection 212 may be in the form of any suitable communications methodology such as RS232 or RS485, USB, Thunderbolt, FireWire, Ethernet, Bluetooth, LiFi, Wi-Fi, $I^2C$, LIN-Bus, CAN-Bus, SPI, etc.

Cables 211 transition from the cold interior 230 of the freezer 100 to the ambient, room-temperature environment 220 of the controller 210. These metal wires 211 conduct heat into the freezer.

Figure 2B:
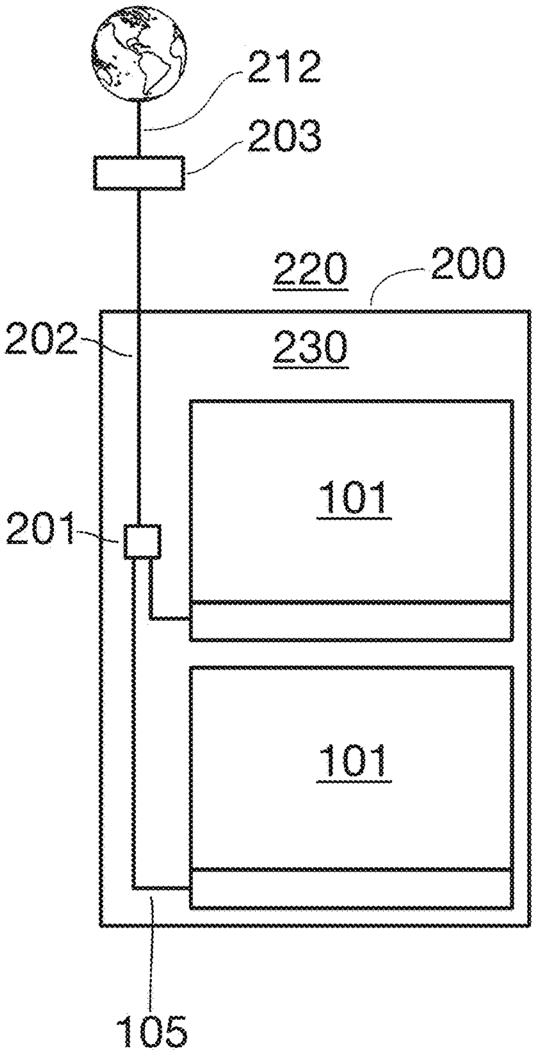

FIG. 2B shows an X-ray side view of a freezer 200 having a reduced heat leak. This is achieved by adding a relay circuit 201 within the freezer's cold interior 230. Relay circuit 201 can be in the form of a suitable multiplexer/demultiplexer. This can significantly reduce the number of wires that need to pass from the system controller 203, at ambient temperature, to the cold interior 230—thus reducing the heat leak and hence the liquid nitrogen boil off rate—a key concern for liquid nitrogen users. If four wires are needed to power and communicate with each shelf this would require 6×4=24 wires for the six-shelf freezer shown in FIG. 1A. Using the arrangement shown in FIG. 1B, only four wires are needed to power and communicate with all 6 shelves. This results in a heat-leak reduction by a factor of 6.

Figure 3:
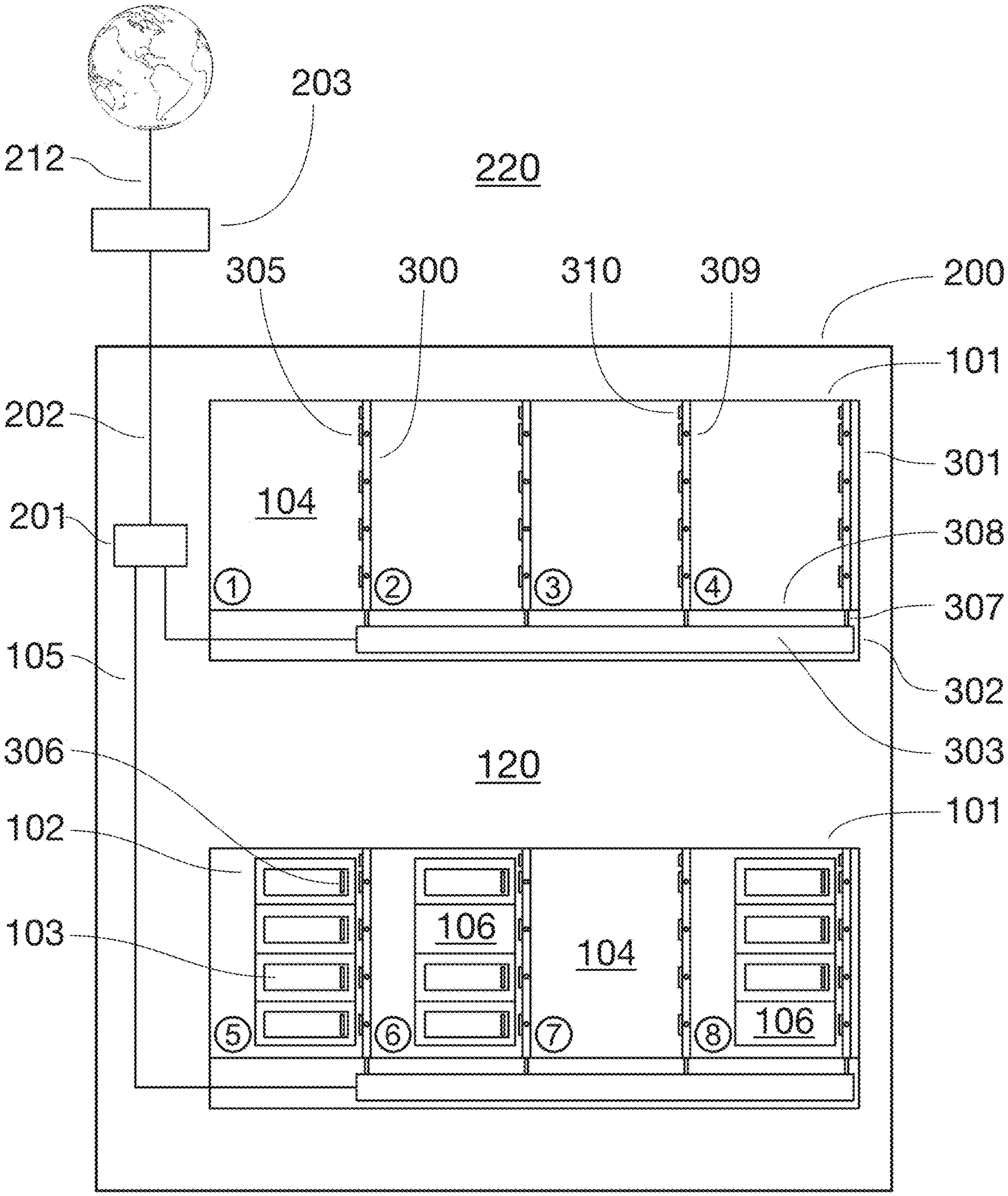
FIG. 3 is a schematic front view of the freezer of FIG. 2B.

FIG. 3 is a schematic front view of the freezer 220 of FIG. 2B as would be seen when looking into the right side in FIG. 2B with two identical shelves 101. In the upright freezers shown in FIGS. 1-3, each rack 102 is typically 1×R×C in format, where R and C are the numbers of rows and columns, respectively, of box locations 106 in the rack 102. In FIGS. 1-3, R=4 and C=3.

In FIG. 3, the upper shelf 101 is shown without any racks 102 for clarity, while the lower shelf 101 is shown with three racks 102 in locations 5, 6, and 8.

Each shelf 101 has two main parts. An upper part 301 with compartments that can accommodate racks 102 and a lower part 302 containing the shelf electronics 303. A divider 308, upon which the racks rest, separates the upper and lower parts.

The upper part 301 has the form of a frame partitioned into four compartments 104. Vertical walls 300 contain electronics that read the box RFID tags 306. They can constitute the right or left wall of each compartment 104. For the particular freezer shown in FIG. 3, the vertical walls 300 are on the right sides of the compartment 104.

Only one rack 102 can be placed in a compartment 104 at a time.

The electronics of the vertical walls 300 connect to the shelf electronics 303 using wired connectors 307.

The vertical walls 300 have RFID read antennae 305, temperature sensors (not shown in this view), rack proximity sensors 310, and indicator lights 309 as will be described below. The number of RFID antennae 305 on each vertical wall 300 is equal to the maximum number of boxes 103 that can be placed in the box locations 106 in rack 102, i.e., 12 for the freezers described in FIGS. 1-4. Each box 103 is tagged with a box RFID tag 306 that uniquely identifies the box.

Each set of shelf electronics 303 receives commands from, and sends data back to, the system controller 203 via a corresponding cable 105. In alternative embodiments, each cable 105 may be replaced or supplemented by a wireless connection.

When a command to read a specific box location is received from the system controller 203, the appropriate RFID antenna 305 is activated by the corresponding shelf electronics 303. The box RFID tag 306 on the box 103 is read by the RFID antenna 305 that is adjacent to it. The box ID information is then sent back from the shelf electronics 303 to the system controller 203 through the relay circuit 201.

Figure 4A:
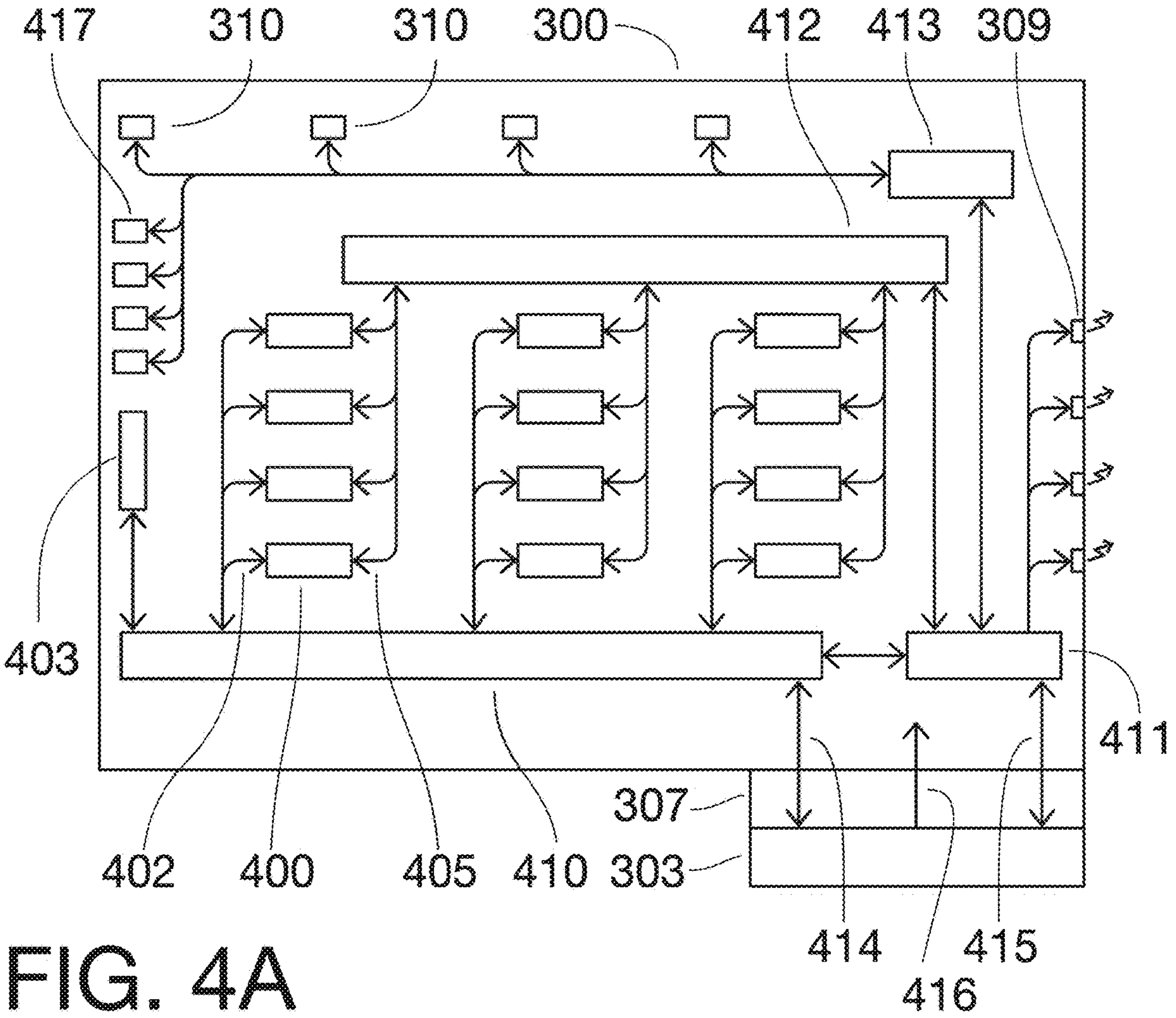
FIG. 4A shows a schematic side view of a vertical wall of the freezer of FIG. 3.

FIG. 4A shows a schematic side view of a vertical wall 300 of FIG. 3 that connects to the shelf electronics 303 via connector 307. FIG. 4A is a representation of the vertical wall functionality. In the interest of clarity, it is not intended to be a correctly scaled representation.

RF signals 414, digital signals 415, and power 416 pass through the connector 307 between the shelf electronics 303 and the vertical wall 300. Power routing within the vertical wall 300 is not shown to reduce the complexity of the figure. The RF signals 414 and the digital signals 415 are two-way signals.

Digital signals 415 provide control to downstream circuits, including, but not limited to, a) setting the state of the indicator lights 309, b) setting the routing instructions (multiplexer state) for the temperature multiplexer 412, c) routing instructions for the multiplexer 410 that routes signals to the RFID antennae, d) reading the rack proximity sensors 310, e) reading the rack code sensors 417, etc. Although they may both be implemented using metal proximity detectors, a rack proximity sensor 310 is used to detect the presence of a rack, while rack code sensors may be used to determine the identity of a rack, as described further below.

Signals from the vertical wall electronics that move upstream back to the shelf electronics 303 can include, but are not limited to, a) temperature data, b) box IDs, c) rack IDs, d) rack proximity data, e) setting confirmations, f) rack code sensor data 417, etc.

The vertical wall 300 contains a number of circuits 400 that is equal to the maximum number of boxes that can be stored in the rack, i.e., 12 (4 rows by 3 columns) for the rack described here. Each circuit 400 is physically positioned so that, as shown in FIG. 3, the RFID read antenna 305 and the box tag 306 are in close proximity when the box and rack are in place.

Figure 4B:
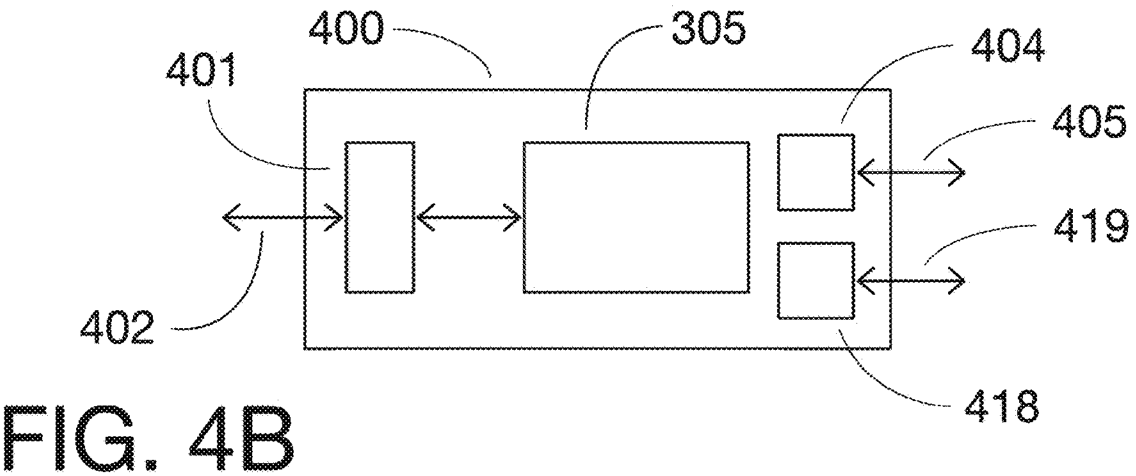
FIG. 4B shows a schematic block diagram of a box circuit for the freezer of FIG. 3.

FIG. 4B shows a schematic block diagram of the box circuit 400 which is repeated at every box location. The box circuit 400 includes an RFID antenna 305 that is connected via a tuning circuit 401. The RFID signal is routed to the correct downstream box location by circuit 410. The upstream signal 414 contains the box RFID information. The shelf electronics 303 can then read the box RFID information from signal 414 and report the box ID back to the system controller 203. In this case, the number of RFID readers is identical to the number of shelves. In another embodiment, the RFID signal 414 can be routed back to the system controller 203 that contains an RFID reader. In this case, the whole system contains only one RFID reader chip.

The existence of a box 103 in a box location 106 can be detected using a sensor 418 that can report the existence of a box 103 to the system via signal 419. The box detection sensor 418 can be in the form of an optical proximity sensor, for example. This can help locate failed RFID tags. The sensors 418, the routing electronics, and the wiring 419 are not shown in FIG. 4A to avoid crowding the figure.

Instructions for addressing the various box locations come from a controller circuit 411 that receives switching instructions 415 from the system controller 203 via the shelf electronics 303. The controller circuit 411 can also have memory (not shown) that can contain a serial number as well as configuration information.

It might be advantageous to identify a rack. One method of doing this is shown in FIG. 4A, where an additional RFID reader antenna 403 is placed so that it can read the ID of the rack that is placed in the compartment 104. This is one possible method of identifying a rack. Another method will be discussed below.

Each vertical wall 300 also contains a number of rack proximity sensors 310 that detect the proximity of a rack. A rack proximity sensor 310 generates an output signal that indicates whether or not metal (e.g., a metal rack 102) is close to the sensor. Consequently, these rack proximity sensors 310 are located adjacent to where metal that forms the rack will be located when the rack is positioned correctly. These rack proximity sensors 310 can be magnetic, optical, or induction based.

While only one sensor is needed to detect the existence of a rack 102 in a compartment 104, a multiplicity of sensors as shown in FIG. 4A can help determine if a rack is being inserted into or if it is being removed from a rack compartment 104. This information can help the sample management software (implemented in the system controller 203) determine what is occurring in real time, in a sample guided access scenario, for example.

When the freezer door is opened, the rack proximity sensors 310 can be continuously polled to determine the state of the sensor. In one embodiment, a polling rate of about 100 Hz should provide all of the information needed to determine if a rack is being removed, inserted, or not being moved at all. A routing circuit 413 polls the rack proximity sensors 310. In different embodiments, the analysis of the proximity sensor data can be used to determine if a rack is being inserted or removed. This analysis can take place in the circuit 413 on the vertical wall 300 or in the system controller 203.

In addition to the rack proximity sensors 310 that can be used to determine rack insertion and removal, rack code sensors 417 (FIG. 4A) can be used to determine the rack configuration as will be explained below.

Referring again to FIG. 4B, the circuit 400 can include a thermometer 404 that is also located adjacent to the corresponding box location. The temperature information from the thermometers 404 are transferred via connections 405 and the temperature multiplexer 412 to the shelf electronics 303. A subset of the circuits 400 can be populated with thermometers 404 depending on how a particular embodiment of the system is realized. The thermometry can be implemented using a platinum resistance temperature detector (RTD), for example. The connection 405 can be in the form of a 2-, 3-, or 4-wire measurement as is needed to achieve the required accuracy.

The rack proximity sensors 310, the rack code sensors 417, the box RFID reader antennae 305, the rack RFID reader 403, the indicator lights 309, and the thermometers 404 can be implemented using multiple printed circuit boards or a single rack-size board. The interconnects such as 402 that carry RF signals can be impedance matched as needed to avoid attenuation of the RF signals. For simplicity, the various signal paths are shown as single lines where in fact they might be carried by multiple wires or printed circuit board traces.

On the vertical wall 300, front-facing indicator lights 309 are used to facilitate guided retrieval as described in the cited patent matters. Activating a particular indicator under the control of the system controller 203 will guide the user to the corresponding row of boxes 103 on the corresponding shelf 101. The indicator lights 309 can be implemented as single- or multi-colored LEDs. They too are controlled by the circuit 411.

The location of the various components can vary in different implementations. For example, the RFID reader chip can be located on the vertical wall shown in FIGS. 3 and 4 or in the shelf electronics 303 or in the system controller 203. The indicator lights 309 can be placed on the lower part of the shelf 302. Wiring complexity, component performance at ultra-low temperatures, optimization of user experience, and cost are some of the considerations that would affect how the components would be distributed throughout the system.

Figure 5:
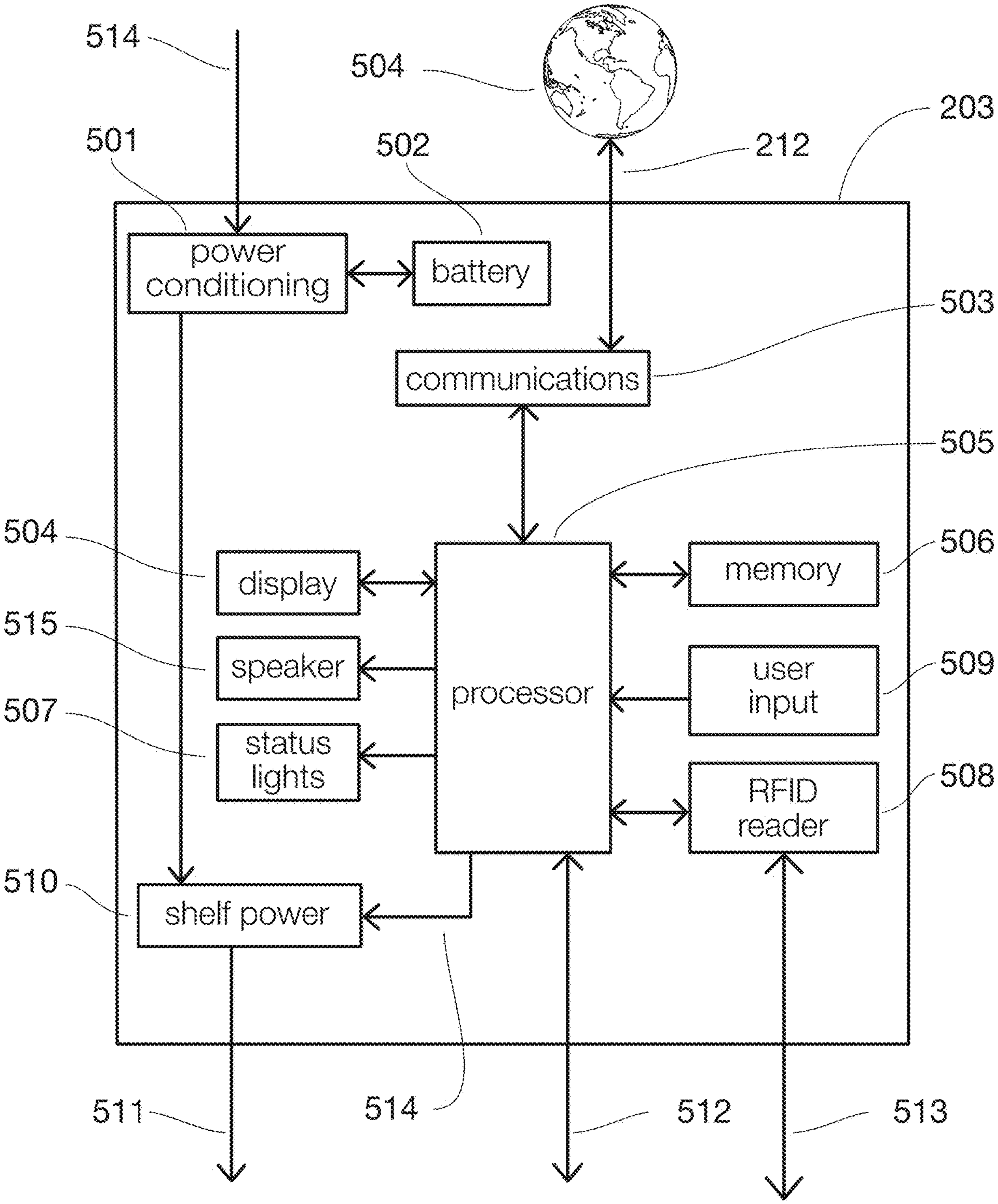
FIG. 5 is a block diagram of one embodiment of the system controller of FIG. 3.

FIG. 5 is a block diagram of one embodiment of the system controller 203 of FIG. 3. The behaviors of the various subsystems of the system controller 203 are managed by a processor 505. The system controller 203 sends data to and receives commands from a sample management system (not shown) through a wired or wireless connection 212. The sample management system is a processor-based system, e.g., a desktop or laptop computer that can be either local to the freezer or in a remote location. It is typically located outside of the freezer and configured to manage the operations of one or more freezers and maintain a database of the samples stored in those freezers. The connection 212 may be in the form of any suitable communications methodology such as RS232 or RS485, USB, Thunderbolt, FireWire, Ethernet, Bluetooth, LiFi, Wi-Fi, etc.

The system controller 203 is powered by a power conditioning circuit 501 which is powered 514 through the mains directly, through a power adapter, or through the connection 212, for example, using power over ethernet. The system controller 203 can also contain a backup battery 502, which can be rechargeable. This power conditioning circuit 501 connects to virtually all of the circuitry in the system. These connections are not shown to reduce the complexity of the figure. However, one connection that distributes power to the freezer is shown—the power distribution circuit 510 conditions power 511 for the shelves 101. The power distribution circuit 510 can be switched off by the processor 505 as needed to reduce power dissipation in the freezer. Alternatively, the shelves 101 can be powered continuously if their power dissipation is sufficiently low.

A communications circuit 503 connects to the outside world 504 via the connection 212. The communications circuit 503 transfers information to and from the processor 505. Examples of data that could flow over the connection 212 are a) rack removal or insertion events, b) inventory requests, c) temperatures, d) rack proximity sensor data, e) locations of the boxes that need to be addressed, f) rack IDs, g) indicator light status, h) user inputs, i) display information, j) rack configuration data, k) shelf configuration data, and l) box IDs.

The processor 505 can have attached memory 506 to store programs, inventory data, and/or data requests, etc. A display 504 can display information to and accept input from the user. Status lights 507 and a speaker 515 can also provide indications to the user. Control switches or buttons 509 can also accept user input and affect the processor's activity as needed.

An RFID reader chip 508 is also controlled by the processor 505. The signal 513 that interrogates the RFID tags can be routed downstream by the relay circuit 201 (FIG. 3) to the different shelves. Alternatively, the routing can be performed in the system controller 210 itself as shown in FIG. 2A. In some embodiments, it might be advantageous for the RFID reader chip 508 to be located in the shelf electronics 303 (FIG. 3). This would bring the RFID reader chip closer to the box RFID chips 306 (FIG. 3).

Digital signals 512 provide control to downstream circuits, including, but not limited to a) routing instructions (multiplexer state) for the relay circuit 201, b) setting the state of the indicator lights 309, c) setting the routing (multiplexer state) for temperature measurements, d) routing instructions for the electronics of the vertical wall 300 for routing signals to the box locations, etc. The digital signals 512 can be sent over any appropriate communications scheme, such as, but not limited to, RS232 or RS485, USB, Thunderbolt, FireWire, Ethernet, Bluetooth, LiFi, Wi-Fi, $I^2C$, LIN-Bus, CAN-Bus, SPI, etc.

Digital signals 512 from the freezer that move upstream back to the system controller 203 can include, but are not limited to a) temperature data, b) box IDs, c) rack IDs, d) rack proximity sensor data, e) setting confirmations, etc.

Signals 511-513 of FIG. 5 are transmitted via connection 202 of FIG. 3.

Figure 6:
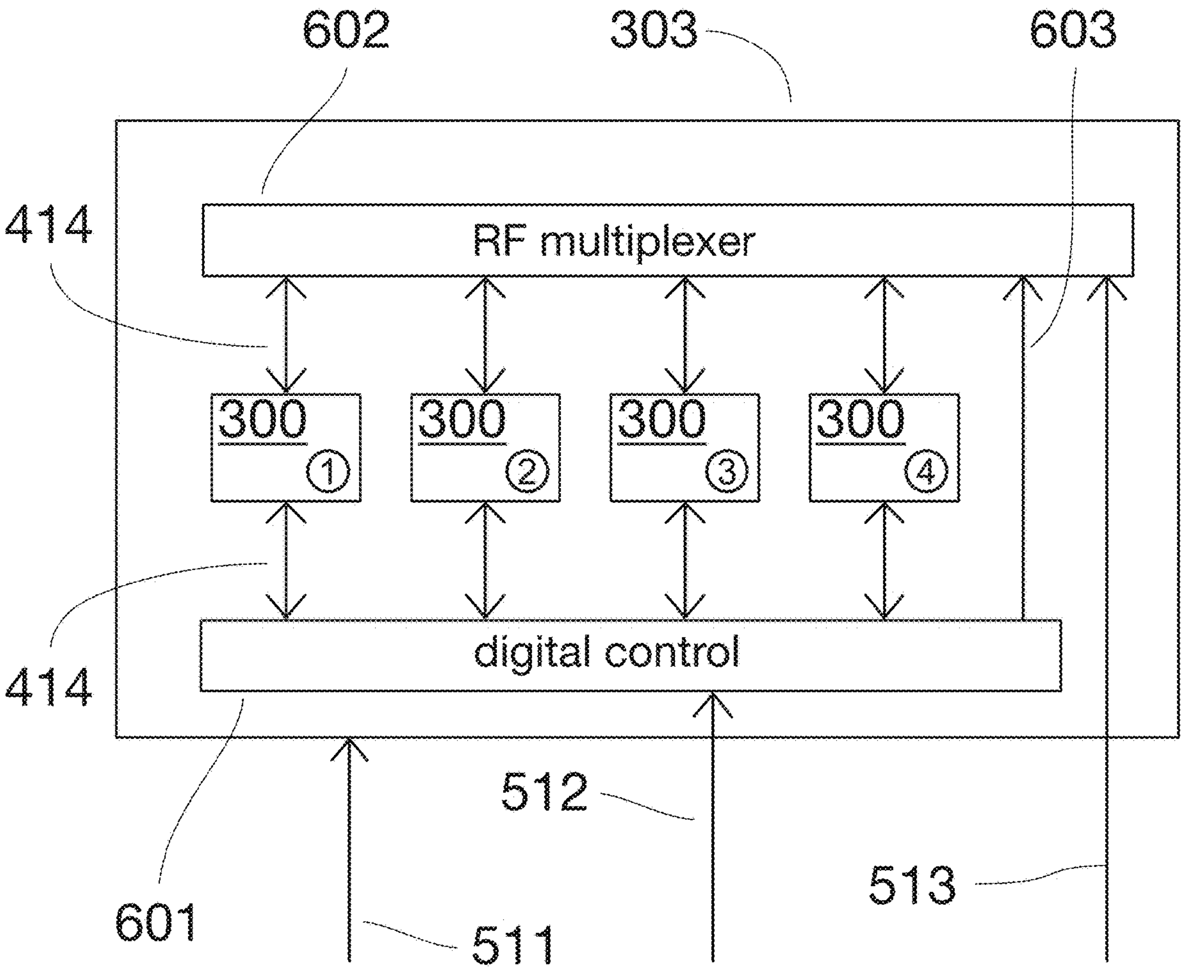
FIG. 6 is a block diagram of shelf electronics for the freezer of FIG. 3.

FIG. 6 is a block diagram of the shelf electronics 303 of FIG. 3. Power 511, digital control signals 512, and RF signals 513 enter the shelf electronics 303 from the relay circuit 201 of FIG. 2B or 3 or from the system controller 210 of FIG. 2A, depending on the particular embodiment chosen.

The details of the distribution of the power 511 in the shelf is not explicitly shown. The power 511 reaches all of the appropriate electronic components as needed.

The RF signals 513 are routed through an RF multiplexer 602 to the various vertical walls 300 that form the right walls (or left walls in a different embodiment) of the rack compartments 104 of the shelves shown in FIG. 3. The top shelf of FIG. 3 has four compartments 104 labeled 1-4. Routing of the RF signals 513 by the RF multiplexer 602 to the vertical wall 300 is controlled by the digital signals 603 coming from the digital control circuit 601. The indicator light control signals, proximity sensor data, temperature data, etc., are also routed in the digital control circuit 601.

Addressing the different rack-reader and shelf electronics can be done using hardwired connections between the shelves and the relay circuit 201 (FIG. 3). Or, in a different embodiment by using various addressing schemes using the digital signals 512 as is common in many digital communication protocols such as RS485, etc. The rack-reader and shelf addresses can be programmed into the circuits 411 (FIG. 4A) and 601 (FIG. 6) or implemented in hardware in the form of circuit components that would make up a specific address.

Figure 7A:
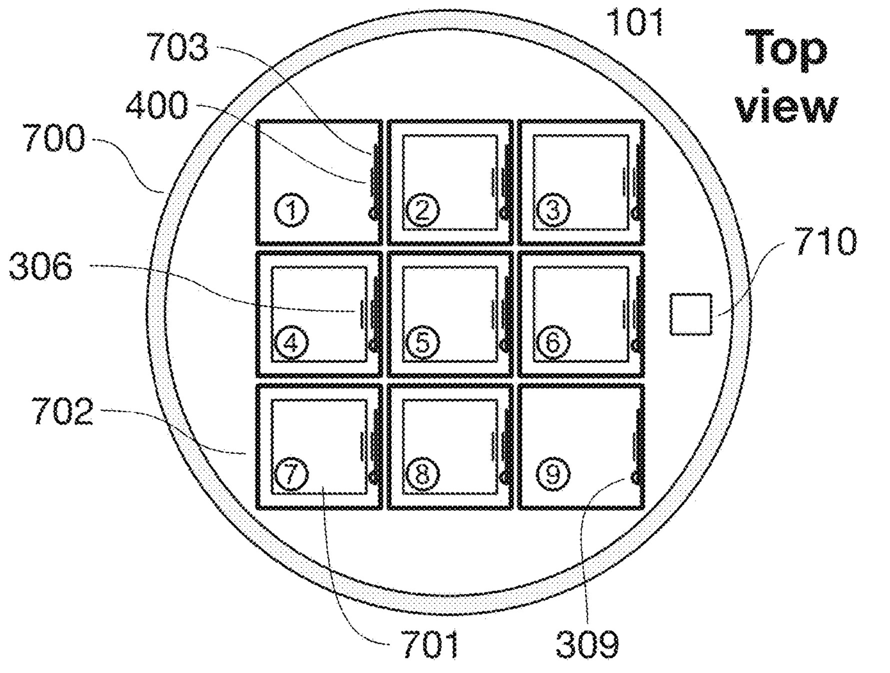
FIGS. 7A and 7B show top and side views, respectively, for a freezer.
Figure 7B:
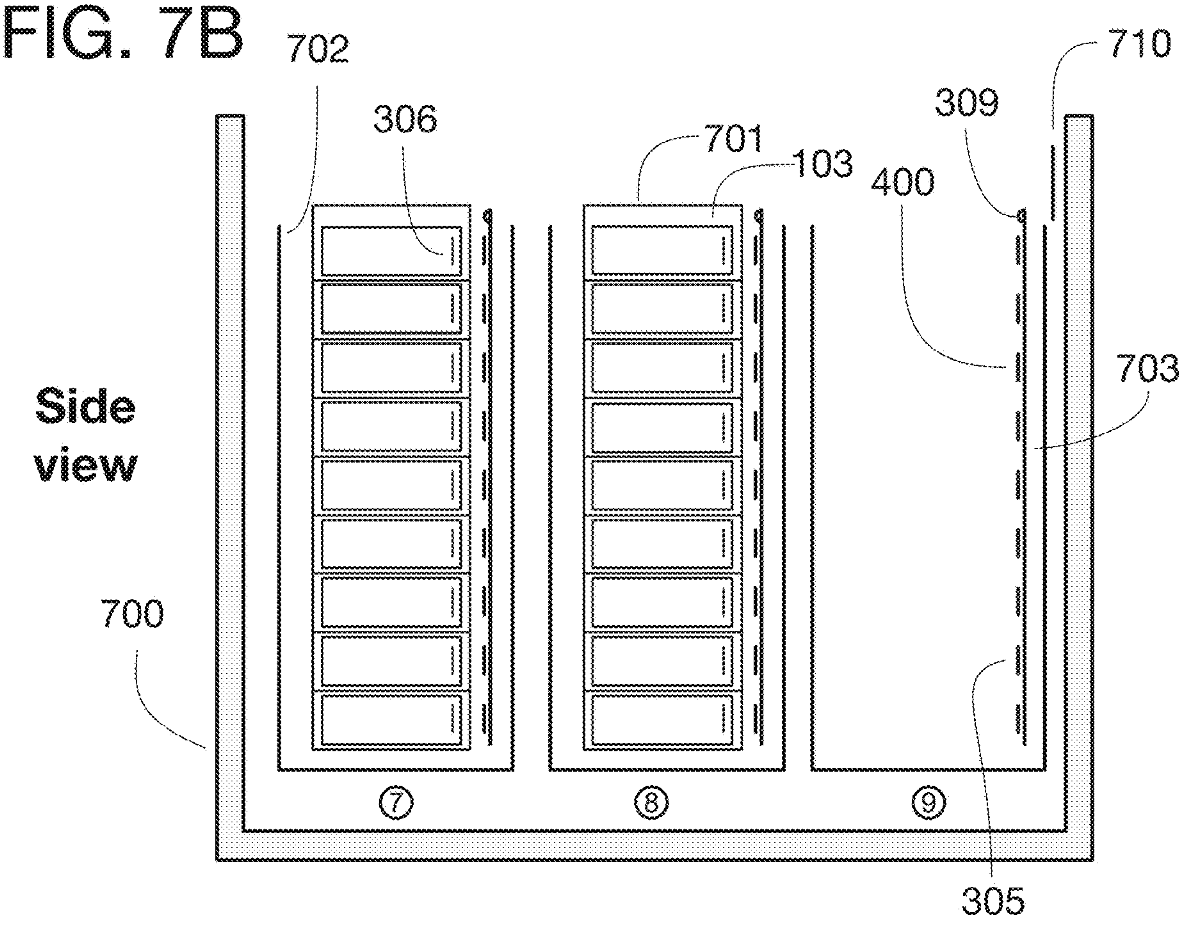

The system described above could be adapted to chest freezers and liquid nitrogen based freezers as shown in FIGS. 7A and 7B. A liquid nitrogen freezer (i.e., dewar) 700 is shown schematically, as a double-walled, vacuum-insulated container (a lid is not shown so that the figure is not unnecessarily complicated).

In freezer 700, the racks are arranged differently from those in the upright freezers depicted in FIGS. 1-4, which are similar in arrangement to a kitchen refrigerator. In a liquid nitrogen or chest freezer, racks are placed vertically, and there are no shelves per se. For chest and liquid nitrogen freezers, such as the liquid nitrogen freezer 700 of FIG. 7, each rack 701 can receive a stack of L boxes 103, where L is the maximum number of boxes. The maximum number L of boxes per rack is typically 4 to 13 for a typical 2" tall box in a typical freezer—L would be scaled accordingly for other box heights.

In the liquid nitrogen freezer 700 of FIG. 7A, the shelves are replaced by nine rack spaces 702, which are arranged as a series of square tubes connected together like a square-lattice honeycomb into which the racks 701 are inserted vertically as shown in FIG. 7B. For clarity, spaces 1 and 9 are shown without racks 701.

All of the characteristics of the shelf design described above and in FIGS. 1-6 for an upright freezer can be transferred to chest and liquid nitrogen freezers. Here, too, for each rack 701, there would be electronics 703, an indicator light 309, and a different box location circuit 400 at each box location with an antenna 305 (not shown in FIG. 7) that reads the corresponding box RFID tag 306, proximity sensors, etc. The external system controller 203, the internal relay circuit 201, and the wiring are not shown in the interest of simplicity.

Similar to the upright freezer arrangement, where the shelf electronics 303 can read multiple columns of boxes 103 through the vertical wall 300, the coplanar electronics 703 in the rack spaces 1, 4, and 7, for example, can be combined into one large circuit board that would control the racks in rack locations 1, 4, and 7.

Fully implemented freezers as shown in FIG. 3 and FIG. 7 can provide real-time inventory, temperature sensing, rack removal and insertion information, and rack IDs.

Figure 8A:
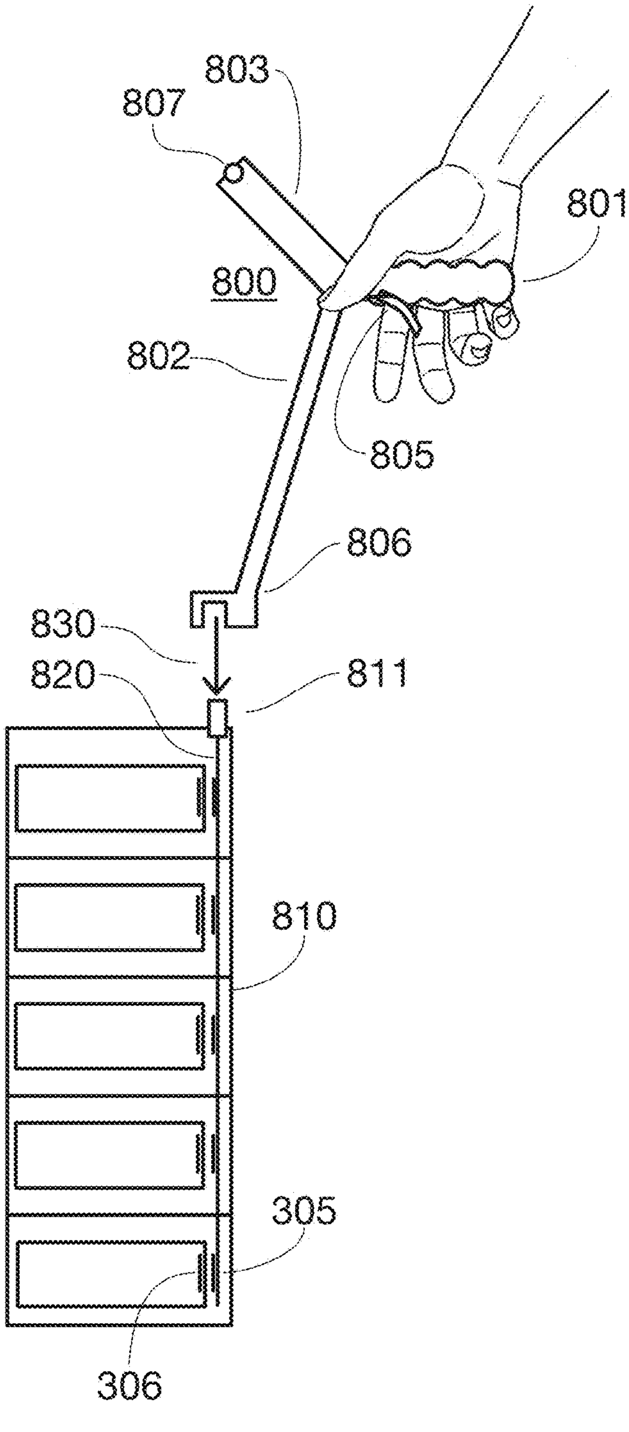
FIGS. 8A-8C illustrate a semi-manual method for inventorying a rack.
Figure 8C:
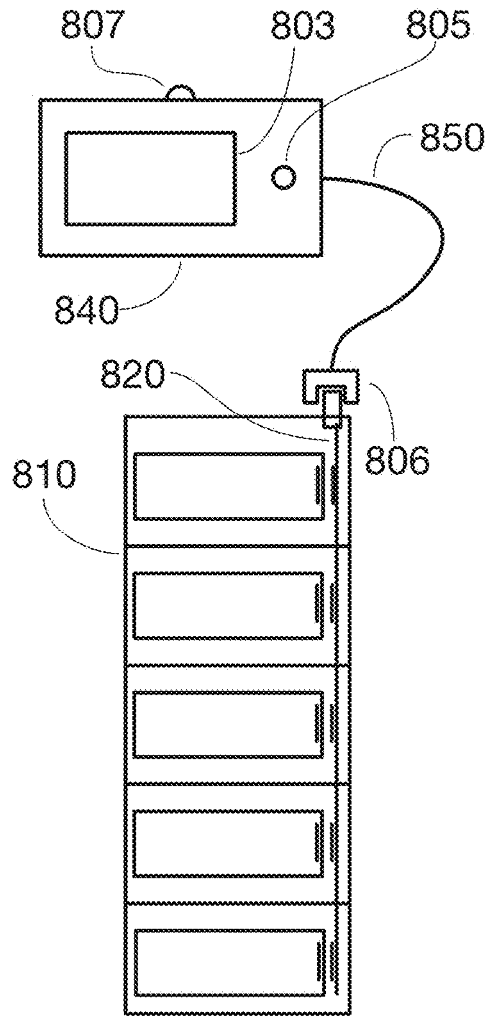
Figure 8B:
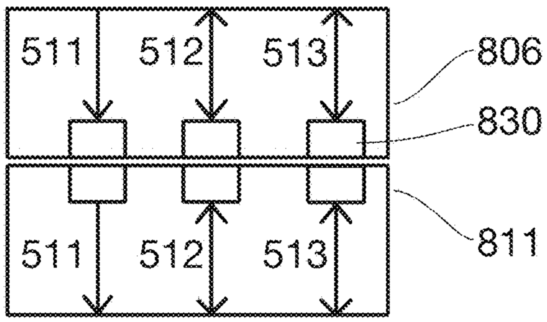

FIGS. 8A-8C illustrate a semi-manual method for inventorying a rack 810. In FIG. 8A, a handheld reader 800 can be used to manually scan the contents of a rack 810. This would eliminate the need to wire the freezer as would be required for the built-in solutions described in FIGS. 1-3 and FIG. 7. Here, the electronics 820, similar to the shelf electronics 303, are located in each rack so most of the complexity of the shelves, as described above, moves to the rack.

In various embodiments the handheld reader 800 can have any or all of these components: a) a grip 801, b) an extension 802, c) a display 803, d) a trigger or pushbutton 805, e) a read head 806, f) an indicator light 807, and g) a wired or wireless connection (not shown).

The arrow 830 shows how the rack dock 811 would be mated to the appropriately shaped read head 806 in the reader 800. In one embodiment, the reader 800 can be constantly polling the read head 806.

Once the read head 806 mates with the rack dock 811, the reader 800 activates the electronics 820 in the rack 810 to determine the rack contents. Alternatively, the electronics 820 can be activated using the trigger 805 input from the user. Triggered rack reads can be used to conserve battery power.

The electronics in the reader 800 can be identical to that of the system controller 203 shown in FIG. 5. The electronics 820 in the rack 810 can be identical to the shelf electronics 303 shown in FIG. 6. Here, too, the rack 810 can report its rack configuration to the reader 800.

In FIGS. 5, 6, 7, the connections 511-513 are hardwired, but the reader 800 is a detachable device. When making the connection between the rack dock 811 and the read head 806, a direct electrical connection would be unreliable because of the ice buildup that is typical in ultra-low temperature freezers.

Hence, the reader 800 would need to connect to the rack 810 without direct electrical (ohmic) contact. The connections for power 511, data 512, and RF 513 are made using non-ohmic connections when the rack dock 811 and the reader head 806 are mated as shown in FIG. 8B.

The connections can be made using any of a variety of schemes such as inductively coupled coils, acoustic signals, optical signals, wireless technologies such as Bluetooth, etc., as was described in cited patent matters. For the sake of simplicity, we will assume in the following discussion that the connection is achieved by inductively coupled coils.

The different signals 511-513 can be communicated through the same physical coils but at different frequencies which can be separated in the electronics using standard filter techniques.

Alternatively, the signals can be communicated in different time slots allowing them to be communicated over the same channel at the same frequency. This is an especially appropriate technique for the RF signals 513 and the control signals 512.

As shown in the embodiment of FIG. 8C, the read head 806 can be separated from the rest of the reader 840 by a cable 850. Otherwise, all of the components can be identical to those discussed above. This arrangement can be useful when trying to locate a box. Once the rack is pulled from the freezer, it can still be attached to the reader. This would facilitate guided access, described in the cited patent matters, because notifications to the user can be made if the wrong box has been removed, for example. In this case, the length of the cable 850 is long enough so that it stays connected even when manipulating the rack to retrieve or insert a box.

The docking mechanism that keeps the rack dock 811 attached to the read head 806 can be a mechanical or magnetic latch. This mating should be such that the rack dock 811 and the read head 806 will firmly remain attached when handled during normal use but can be easily separated when needed.

The reader 800 can be used in an upright freezer as well with the appropriate racks. In this embodiment, the freezer would not need any modifications at all—only the racks would need to be replaced with racks that contain the electronics similar to the electronics 820.

One advantage of the embodiment shown in FIG. 8 is shown in FIGS. 9A-9B. A handheld reader 800 can be used to manually scan individual racks 810 that are randomly arranged in a freezer as shown in FIG. 9A. The advantage of this is that no a priori organization needs to be established for the freezer and that racks of different sizes can be inserted as needed into the freezer. The upstream database can store information about the freezer contents as it is collected.

The freezer can also have an identification circuit 901 that identifies itself to the handheld reader 800. This can be done in any number of ways including but not limited to: a) using a wireless signal such as Bluetooth that connects when the reader 800 is brought in close proximity to the freezer, b) using a dedicated RFID tag that can be read by a dedicated RFID reader circuit (not shown) in the reader 800, and/or c) using a rack dock 811 that is similar to those on the racks as shown in FIG. 9. Mating the reader head 806 (FIG. 8A) to the rack dock 811 of the ID circuit 901 will read an ID that uniquely identifies the freezer.

To perform a freezer inventory using the reader 800 shown in FIGS. 8 and 9, each rack 810 is read in turn. This implies that the accuracy of the inventory is based on the behavior of the user. For example, if the user forgets to read the contents of a rack, then the inventory will not be accurate. When guided access to the boxes is used, as described in the cited patent matters, the user can read each rack in turn and be alerted to the fact when a required sample is in the rack that is currently being read.

In another embodiment, shown in FIG. 10, each rack 810 is connected to a read head 1001. Here, too, the organization of the freezer can be ad hoc, i.e., the racks are not constrained to specific locations or sizes—as is shown in FIG. 9A.

With this arrangement, an inventory can be performed without opening the freezer 700 (again the freezer is shown in FIG. 10 without a lid for simplicity). Each rack 810 is attached at its rack dock 811 to a read head 1001 that is connected to a relay circuit 201 that accepts read commands and power from a system controller 203 and distributes the commands and the power internally in the freezer. The system controller 203 is connected, as before, to the upstream inventory control software (not shown). Information from the racks is returned through the relay circuit 201 as well.

For clarity, one of the read heads 1001 (on the left) is shown not yet docked to a rack. The docking mechanism that keeps the rack dock 811 attached to the read head 1001 can be a mechanical or magnetic latch such that rack dock 811 and the read head 1001 can be separated when needed but they will remain firmly attached when handled during normal use.

In the case of guided access, discussed in the cited patent matters, an indicator light 1002 can show the user what rack to remove while in the process of retrieving a particular box. The indicator light 1002, possibly in the form of an LED, can be single- or multi-colored to indicate more than one thing to the user.

Figure 10A:
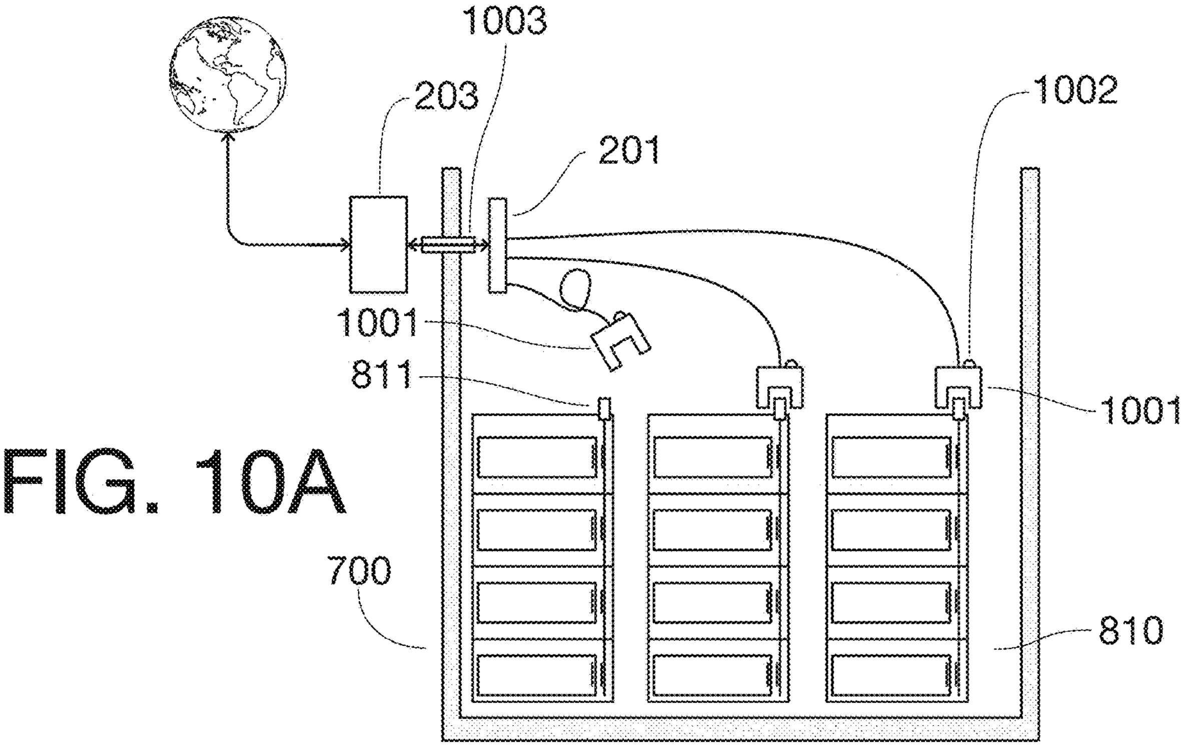
FIGS. 10A and 10B illustrate an automatic method for inventorying a freezer.
Figure 10B:
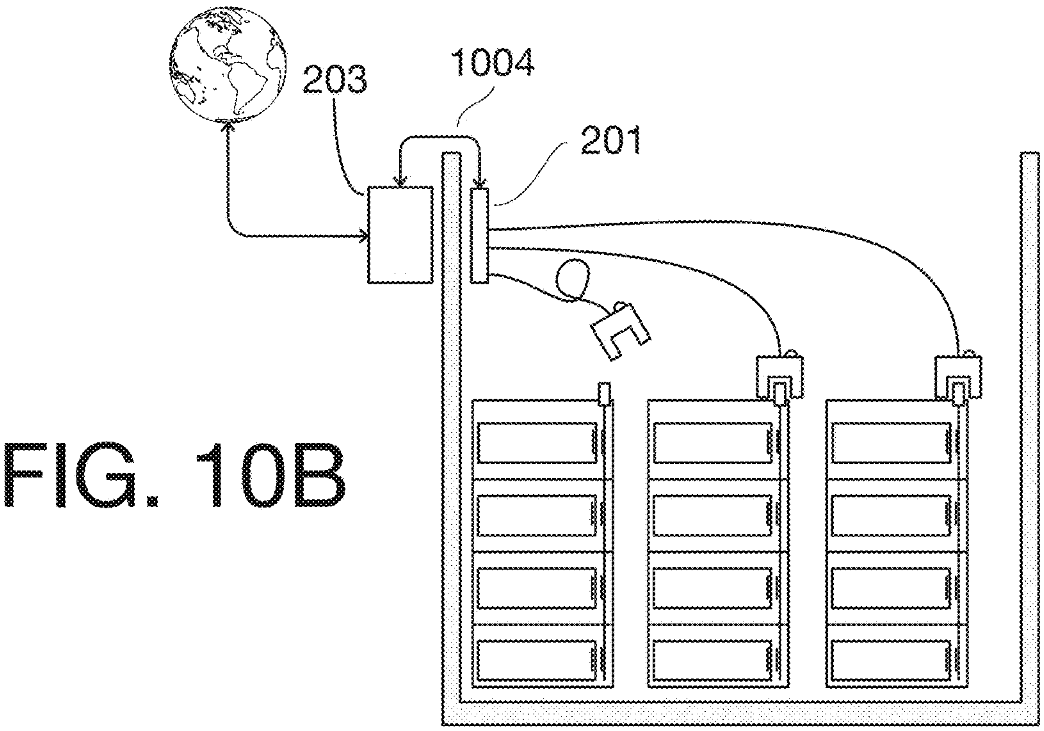

The external system controller 203 is connected to the relay circuit 201 via a vacuum feedthrough 1003, shown in FIG. 10A, that connects the inside and the outside of the freezer. Alternatively, in another embodiment shown in FIG. 10B, the connection between the system controller 203 and the relay circuit 201 can pass through the opening of the freezer. The embodiment shown in FIG. 10B has the advantage of using an existing freezer as-is—there is no need to modify the freezer in any way. This can be very useful when retrofitting the inventory system described herein to an existing liquid nitrogen freezer.

In FIGS. 8-10, the racks are not simply folded and welded sheet metal—they contain antennae, thermometers, read electronics for multiplexing between the different box locations, etc.

Figure 11A:
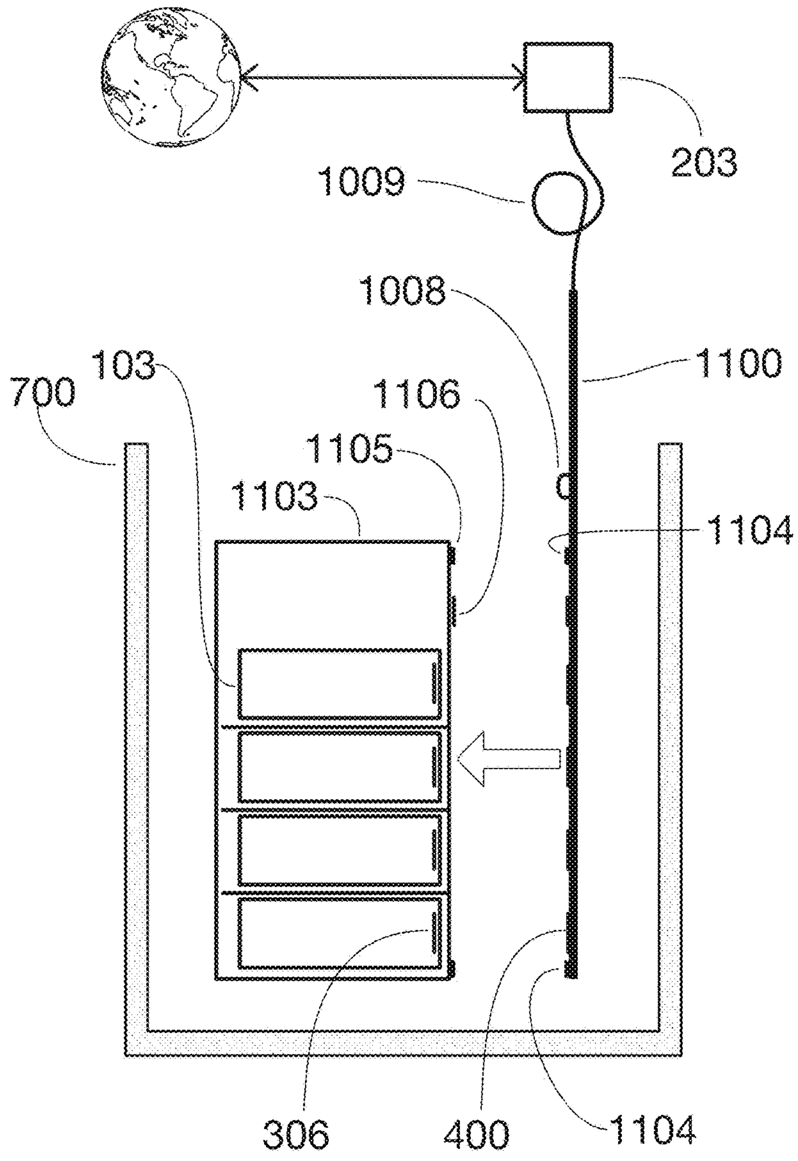
FIG. 11A illustrates a method for inventorying a freezer using a wand reader.
Figure 11B:
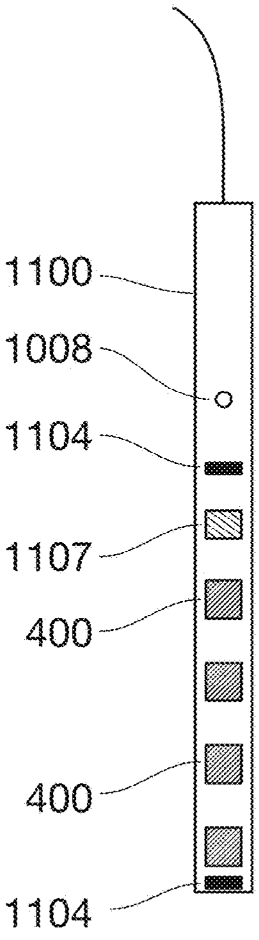
FIG. 11B shows a front view of the wand reader of FIG. 11A.

In another embodiment shown in FIG. 11, the rack 1103 is read by a removable reader 1100 in the shape of a tethered wand shown edge-on in the freezer 700 in FIG. 11A and face-on in FIG. 11B. The wand reader 1100 connects to the system controller 203 via cable 1109. Box circuits 400 are located on the wand reader 1100 such that the box RFID tags 306 are read by mating the wand reader 1100 to the rack 1103.

This method of reading the rack contents can be useful when searching for samples. A common method used when manipulating samples is to put the rack in a handling container that is cooled with dry-ice or liquid nitrogen (a CryoCart is a commercially available version of this). This is used to prevent the samples from warming while they are out of the freezer. Since the rack is no longer in the freezer, its contents can no longer be tracked. The system shown in FIG. 11 would allow tracking the boxes while the rack is out of the freezer and in the cooled handling container. Here the rack is shown standing up to be consistent with the other dewar-based figures but, in the case of a cooled handling container, the rack would typically be horizontal.

Proper positioning of the wand reader 1100 relative to the rack 1103 is critical so that the box RFID tags 306 and the RFID read antennae 305 (in the box location circuits 400) are correctly aligned. This alignment can be achieved using mechanical means such a slots (not shown), tracks (not shown), and/or magnets 1104 that are placed at various locations on the wand. The rack 1103 has its own magnets 1105 in places that match those of the wand magnets 1104. The magnets 1104 and 1105 should be strong enough to position the wand reader 1100 properly relative to the rack 1103 and remain attached when handled but weak enough so that the wand reader 1100 can be easily removed. The wand magnets 1104 or the rack magnets 1105 (but not both) can be replaced by a magnetic material.

A wand in the form of a single strip of box ID antennae is presented here. Specifically, the wand shown in FIG. 11 is a 5×1 antenna array. In other embodiments where the rack is an N×M array of box cells, the wand would have the form of a panel that can read N×M boxes. The concept is the same for the panel array. For example, instead of there being a 5×1 antenna array for the rack shown in FIG. 11, there would be a 4×3 antenna array for the racks shown in FIG. 2.

In FIG. 11A, the rack 1103 and the wand reader 1100 are shown separated for clarity. In practice, the rack 1103 would be read when the magnets 1104 and 1105 are in contact. The manipulation of the wand reader 1100 indicating the positioning of the wand for reading is indicated by the arrow in FIG. 11A.

One advantage to this embodiment is that the rack 1103 itself has no electronics, unlike racks 810 of FIG. 8, which have rack electronics 820. Here the system controller 203 does not need multiplexers other than those needed to switch between the box locations 400.

In the embodiment shown in FIG. 11, the rack 1103 has an RFID tag 1106 of its own that identifies the rack to the database. This also allows a particular box 103 to be associated with a particular rack 1103 in the data base. The rack RFID tag 1106 can be associated with a dedicated read antenna 1107 on the wand reader 1100.

Figure 12:
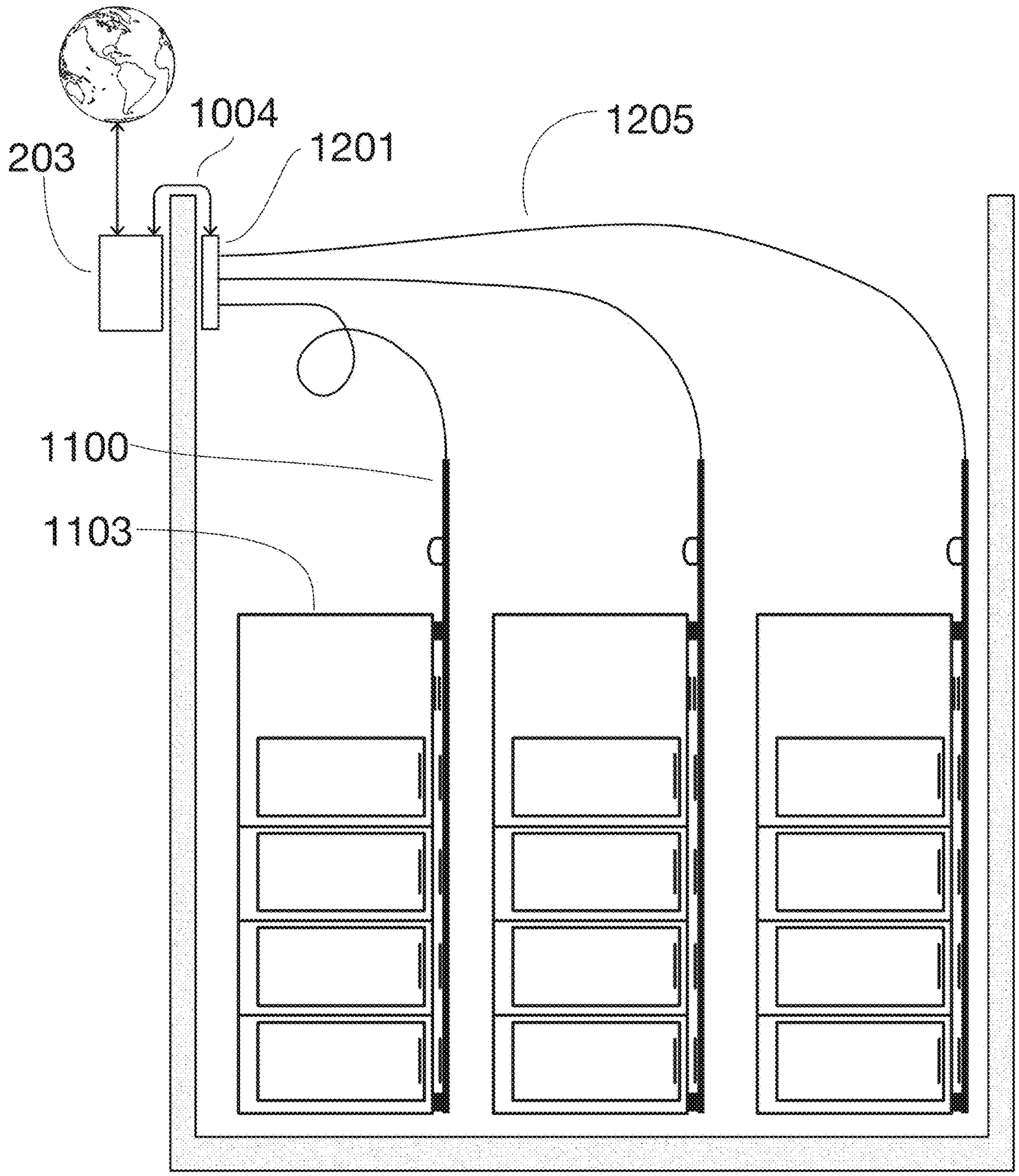
FIG. 12 illustrates an automatic method for inventorying a freezer using multiple wand readers.

FIG. 12 shows another embodiment where multiple wand readers 1100 are connected to multiple racks 1103 with cables 1205 that connect via the relay circuit 1201 to the system controller 203. The wand reader 1100 can also have an indicator light 1008 to show the user that the correct rack 1103 has been located when using the guided access protocols described in the cited patent matters.

There are two main types of liquid nitrogen freezers. Those with straight walls as shown in FIG. 7, for example, and those with a smaller access opening as shown in FIG.

13. The freezer 1300 shown in FIGS. 13A-C has an opening 1301 that is smaller than the diameter of the freezer and offset from the center of the freezer. FIG. 13A is a side view of the freezer in cross section. This configuration is used to reduce the heat leak into the freezer which results in a lower boil-off rate for the liquid nitrogen.

The systems described in FIGS. 7-12 can be installed in freezer with a narrow opening without the need to modify the freezer in any significant way with the possible exception of implementing a feedthrough 1003 (FIG. 10A).

The racks 1302 sit on a rotating platform 1303 in the freezer (similar to a "Lazy Susan"). This platform 1303 rotates on a spindle 1304 allowing access to all of the racks as they rotate below the access port 1301. This platform keeps the racks in the cold nitrogen vapor but above the liquid nitrogen 1305 itself. Other freezers may have different spindle and rotating platform construction but in principle they are functionally the same.

The racks can be functionally similar to any of the designs in FIGS. 8, 9, and 11 and do not require permanent wiring in the freezer. A hidden rack 1302 is simply rotated into an accessible position (as shown in FIG. 13B) and read through the access hole 1301.

Figure 13B:
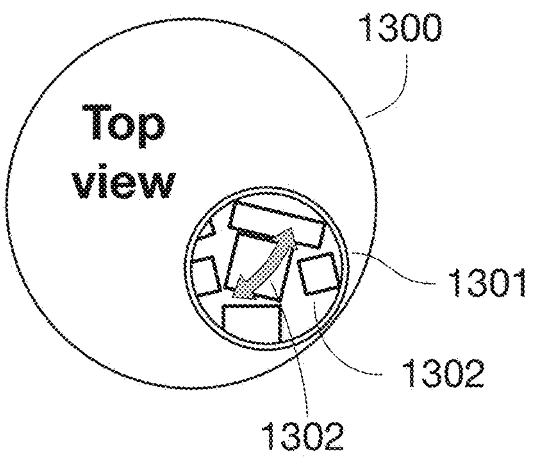
FIGS. 13A and 13B show side and top views of a freezer.
Figure 13C:
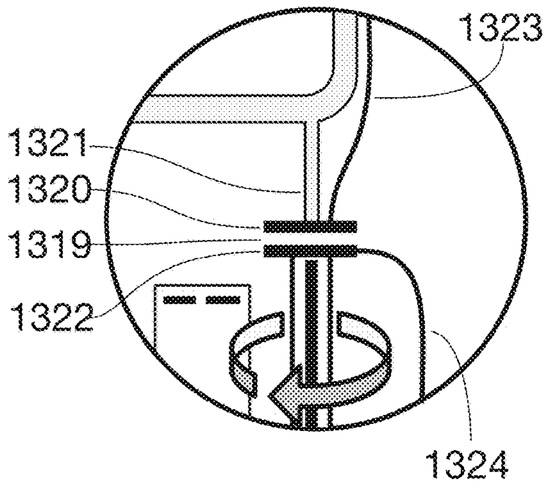
FIG. 13C shows a detail of an alternative embodiment of the freezer of FIGS. 13A and 13B.
Figure 13A:
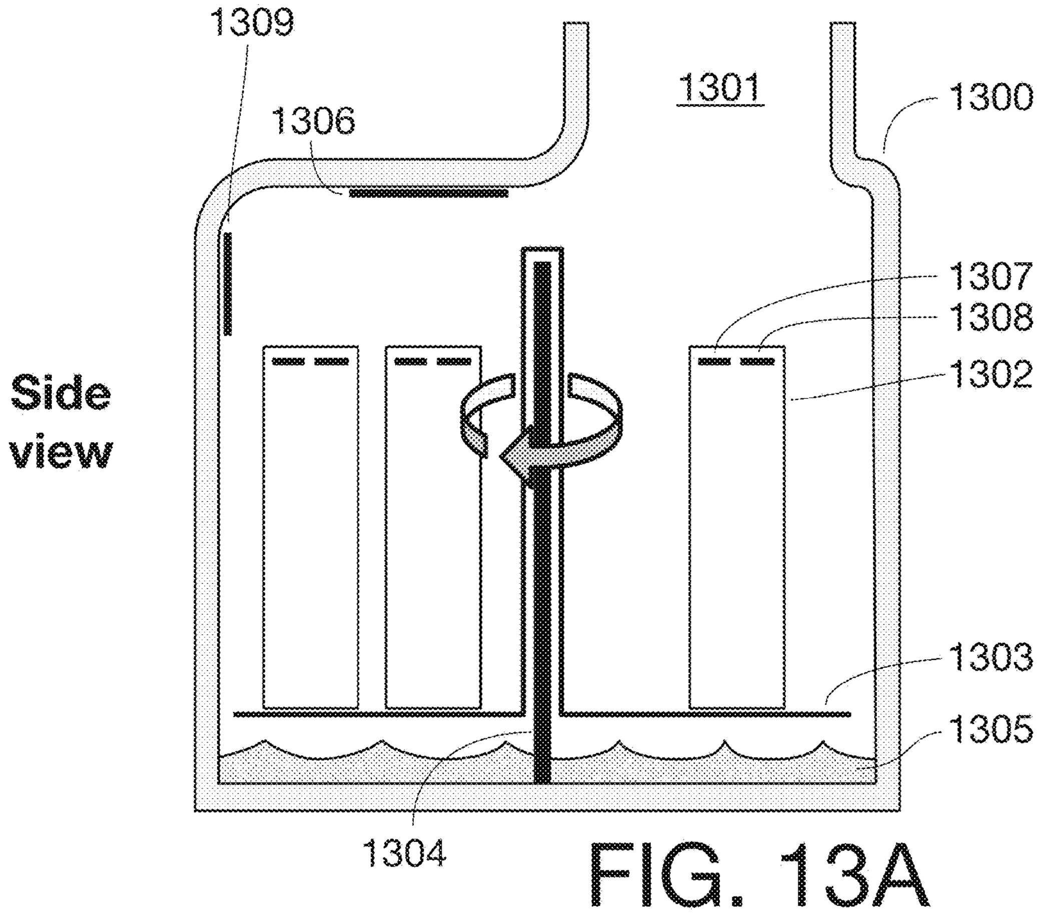

However, the implementations shown in FIGS. 7, 10, and 12, cannot be directly transferred to a freezer of the type shown in FIG. 13A and FIG. 13B, because the cabling required needs to rotate as the platform 1303 is being rotated when accessing the racks 1302.

One way to avoid this problem is to not let the platform rotate through a full 360° but limit the rotation to less than 360° with an appropriate mechanical stop. In this arrangement, the cabling (not shown) would wind and unwind when the platform 1303 is being rotated clockwise and counter-clockwise. This solution requires that the cabling be flexible at the extremely cold temperature of liquid nitrogen (−196° C.). Designing cables that can operate for years under constant flexing at ultra-low temperatures is challenging. In addition, the cables themselves conduct heat into the freezer resulting in an increase in the liquid nitrogen boil off.

Another way to address the issue of having electrical connections passing between the stationary freezer and the rotating platform is to use a commutator. This may be impractical because of the need to seal the contacts in an ultra-low temperature environment and the ice in the freezer which just gets worse over time.

In another embodiment, as indicated in FIG. 13A, the freezer 1300 can have an antenna 1306, located somewhere in the freezer that transmits power to the internal space of the freezer when an inventory is being performed. The orientation of antenna 1306 is optimized to allow the best reception by each of the racks 1302. Each rack 1302 can harvest some of the energy transmitted by antenna 1306 using a circuit 1307.

Data to and from each rack 1302 can be transmitted back and forth from an antenna 1308 on the rack 1302 to an antenna 1309 in the freezer using any appropriate wireless standard such as 802.11, BlueTooth, Zigbee, etc.

In some embodiments, antennae 1307 and 1308 can be implemented as a single antenna, and antennae 1306 and 1309 can be implemented as a single antenna.

The location and orientation of the antennae 1306, 1307, 1308, and 1309 can be such that the optimum power transmission and data integrity will be maintained. In FIG. 13A, the antennae are shown in non-optimal orientations and locations for the sake of clarity. The energy harvesting techniques are well known and will not be repeated here.

In one embodiment, each rack 1302 can transmit at a specific time slot to avoid collisions in the data stream. In another embodiment, each rack 1302 can transmit at random times at very low duty cycle thus avoiding collisions in the data stream from multiple racks. In the rare case of a data collision caused by multiple racks transmitting simultaneously, the occurrence can be detected in the data itself, as incorrectly formatted data, for example, and disregarded.

In another embodiment shown in FIG. 13C, an air gap 1319 can be built between the rotating platform 1303 and the stationary freezer 1300. The details of the construction are for illustration only—the exact implementation will depend on the particular freezer construction. In this embodiment, a circular stationary coil 1320 is supported 1321 so that it is concentric to the axis of rotation of the rotating platform. Another coil 1322, also concentric to the axis of rotation of the platform 1303, is inductively coupled to the stationary coil 1320. A stationary cable 1323 connects to the external system controller 203 (not shown). A second cable 1324 that rotates with the platform connects to the compartments 702 or the relay circuit 201 or 1201, depending on the implementation which is being used. The air gap also reduces the conduction of heat from the outside to the internal space of the freezer. There can be more than one coil for separating the power, control, and RF signals as needed.

Optical connections in the form of modulated LED signals and receivers can also be used for the RF and control data.

The shelf electronics 303 (FIG. 3) can also report back to the system controller 203 information about its own configuration, for example, whether the shelf electronics 303 is compatible with 4×5 racks with 2" tall boxes or 3×5 racks for 3" tall boxes. This will allow the system to alert the user if a rack that is incompatible with this shelf was inserted.

Figure 14A:
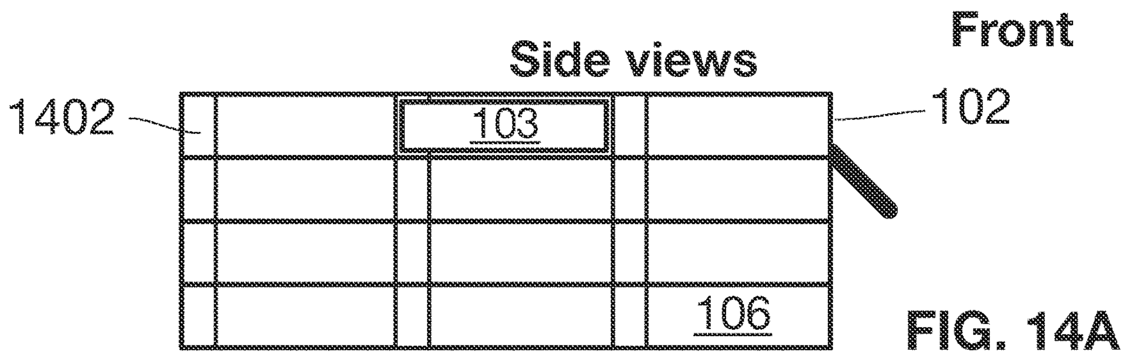
FIG. 14A shows a side view of a first type of rack.

FIG. 14A shows how the rack code sensors 417 can be used to encode information about the rack 102 without the need for any electronics in the rack.

We will discuss two types of information that can be encoded. First, using this technique, a rack 102 having no electronics can report its rack configuration to the shelf electronics 303. As used herein, the term "rack configuration" refers to the number of rows and columns and box sizes of the rack.

In the embodiment shown in FIG. 14A, the vertical wall can identify the rack configuration of the rack. In addition to the rack proximity sensors 310 that were described above and are used to detect the rack insertion and removal, the vertical wall can have an additional set of rack code sensors 417 (see FIGS. 4 and 14B) that can detect notches or holes in the rack's sheet metal. Here these rack code sensors 417 are shown offset to the left by the distance "d" for clarity (see lower left of figure). In reality, the rack code sensors 417 would be behind the holes 1403 once the rack 102 is in place (i.e., d=0).

This will allow the system to detect a mismatch between the rack configuration (number of rows and columns and box size) and the vertical wall 300. If this happens, the user can be alerted to the fact that the rack was put into a rack position 104 that is inappropriate for this rack, even if it fits. For example, a 4 row rack of 2" tall boxes such as that shown in FIG. 14B will be about the same height as a 2 row rack of 4" boxes such as that shown in FIG. 14C but the vertical walls 300 will be different because the antenna array as shown in FIG. 4 will be different. By reading the rack configuration this mismatch can be detected and corrected.

Figure 14B:
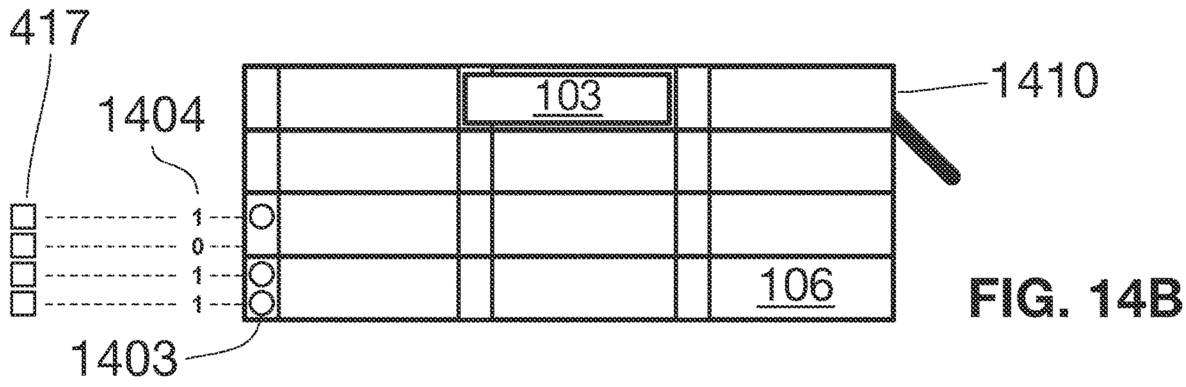
FIG. 14B shows a side view of a second type of rack.
Figure 14C:
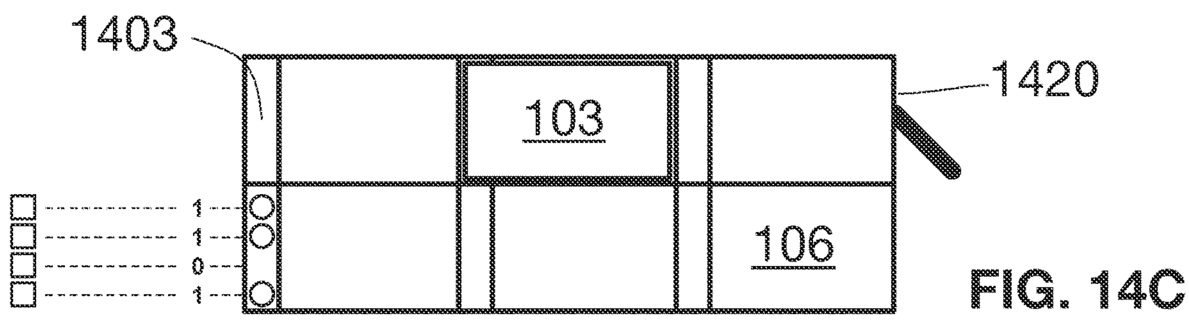
FIG. 14C shows a side view of a third type of rack.
Figure 14D:
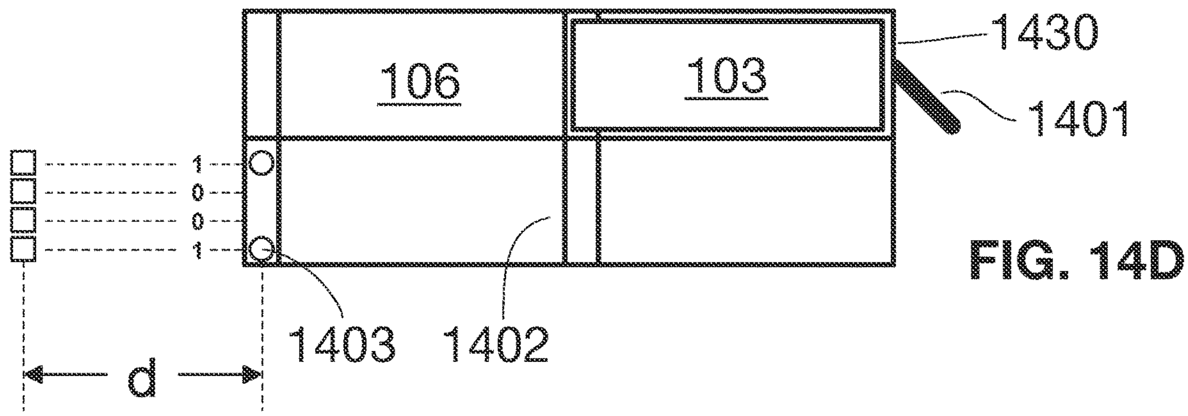
FIG. 14D shows a side view of a fourth type of rack.

The holes 1403 can be used to build a code for the rack configuration in the following way. FIG. 14B shows a 4-bit code 1404 for simplicity. This will allow for 16 different rack configurations, but this can be extended by adding more bits to the code, if needed. In addition, parity bits and error correction can be added if needed.

FIGS. 14A-D shows side views of several racks including a rack 102 (FIG. 14A) that does not have the encoding in place, a rack 1410 (FIG. 14B) that has a 4×3 (row×column) rack configuration, a rack 1420 (FIG. 14C) that has a 2×3 rack configuration, and a rack 1430 (FIG. 14D) that has a 2×2 rack configuration. A handle 1401 is shown on the front end of FIG. 14D to orient the reader. A box 103 is shown occupying the second box location 106 from the back on the top row of each rack type (FIGS. 14A-D).

FIG. 14A show a 3×4 rack 102 with no rack configuration coding. The metal fold 1402 is typical in stainless steel rack design and is used to strengthen the rack. It is also used as a stop so a box 103 will not fall out of the back of the rack 102.

FIG. 14B shows a 3×4 rack 1410 similar to the rack 102 in FIG. 14A but with rack configuration coding in the form of holes 1403 in the vertical sheet metal bend at the back of the rack 1410 that uniquely identifies the rack configuration of rack 1410. If the existence of a hole is interpreted as a logical 1 and the absence as a logical 0, then, reading from top (most significant bit) to bottom (least significant bit), the 3×4 rack 1410 shown in FIG. 14B has a rack configuration code of $\mathbf{1011}_2$ (that is, in binary, or base 2) or 11 (decimal, or base 10). The binary representation is shown in FIG. 14B at reference 1404. Similarly, the 2×3 rack 1420 in FIG. 14C has a rack configuration code of $1101_2$ or 13, and the 2×3 rack 1430 in FIG. 14D has a rack configuration code of $1001_2$ or 9. The exact codes for a given rack configuration is not important as long as they are unique and known to the system.

These holes 1403 can be made during the manufacturing process since the rack configuration code will never change for a given rack. For example, the sheet metal parts are often cut using a laser and then folded and spot welded to form the rack. The holes or notches can be cut into the parts when the parts are cut, even before the rack is assembled. This will add almost no cost to the rack. This allows the rack not to contain any electronics while still allowing the rack to report its rack configuration code when used with suitable reading electronics and rack code sensors 417 shown in FIG. 4A. All of the racks with a particular rack configuration would have one code that corresponds to that rack configuration.

This scheme can be used for upright as well as chest freezers or liquid nitrogen-based freezers. The arrangement of the rack code sensors 417 can be vertical or horizontal depending on the design. FIG. 4A shows a vertical arrangement of the rack code sensors 417.

An extension of this concept can be used to provide each rack with a unique ID. 20 holes or notches can provide about a million unique IDs ($2^{20}$)—far more than the number of racks in a biobank. Since the laser cutter described above is under computer control, cutting unique holes patterns is not difficult to do. In this scenario, the number of unique hole patterns would correspond to the number of racks.

Finally, there is nothing to prevent combining the rack configuration and unique ID information into a longer code that includes both types of information. Using the examples given above, the combined code would be 24 bits long.

Figure 15:
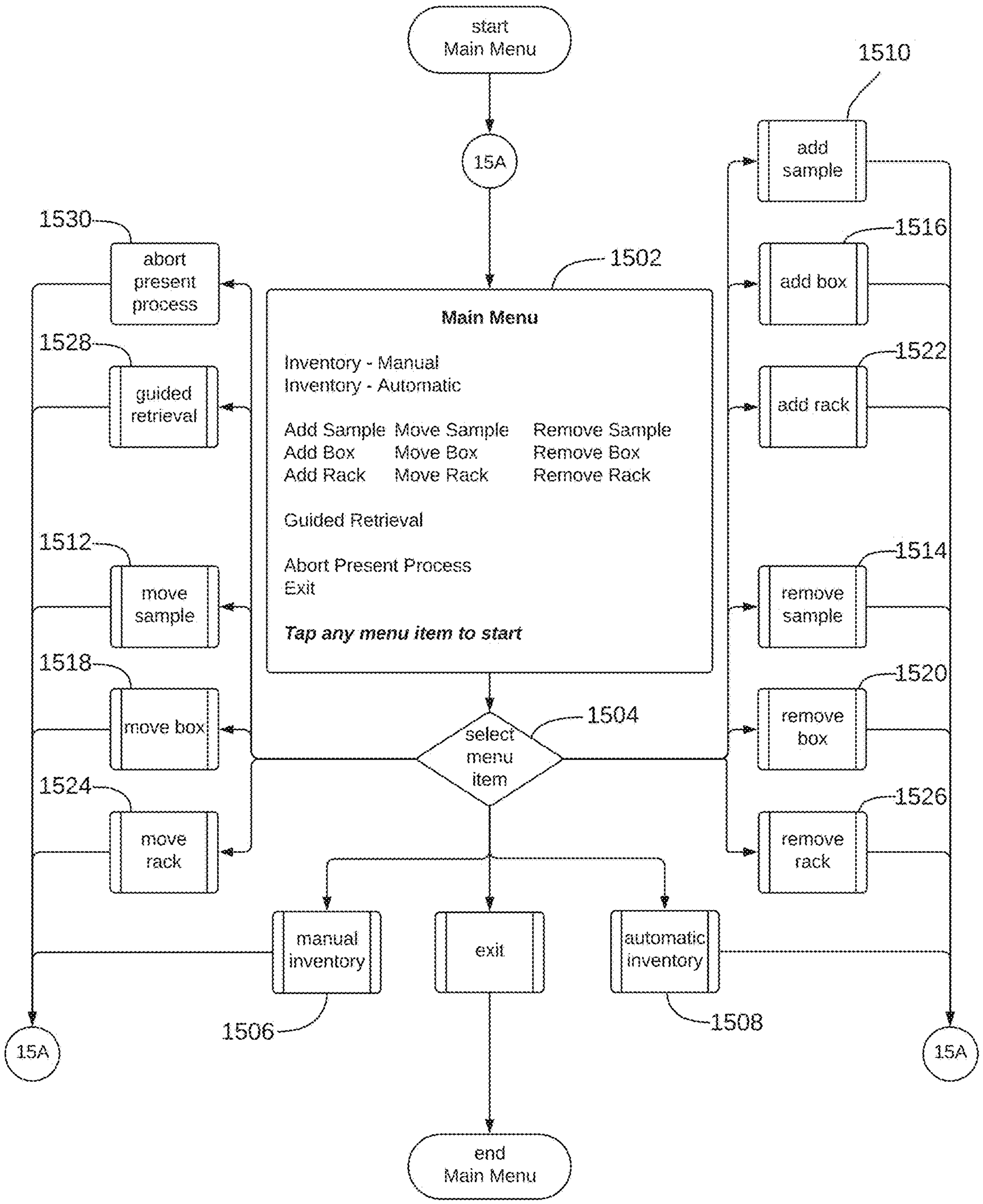
FIG. 15 shows a high-level flow diagram of the processing performed for a cold-storage system according to one embodiment.

FIG. 15 shows a high-level flow diagram of the processing performed for a cold-storage system according to one embodiment. The user can use the main menu 1502 displayed at the system controller (e.g., 210 of FIG. 2A or 203 of FIG. 2B) to choose (1504) from the following operations:

- Perform (1506) a manual inventory for the systems described in FIGS. 9 and 11;
- Perform (1508) an automatic inventory for systems described in FIGS. 2-7, 10-13;
- Add (1510), move (1512), or remove (1514) a sample in the collection;
- Add (1516), move (1518), or remove (1520) a box in the collection;
- Add (1522), move (1524), or remove (1526) a rack from the collection;
- Perform (1528) a guided retrieval of one or more samples; and
- Abort (1530) present operation and exit program.

Once a selected operation is complete, the user is again returned (15A) to the main menu. Note that the database maintained at the system controller that maps samples to their corresponding locations is updated by the system controller for each of operations 1510-1528.

Figure 16:
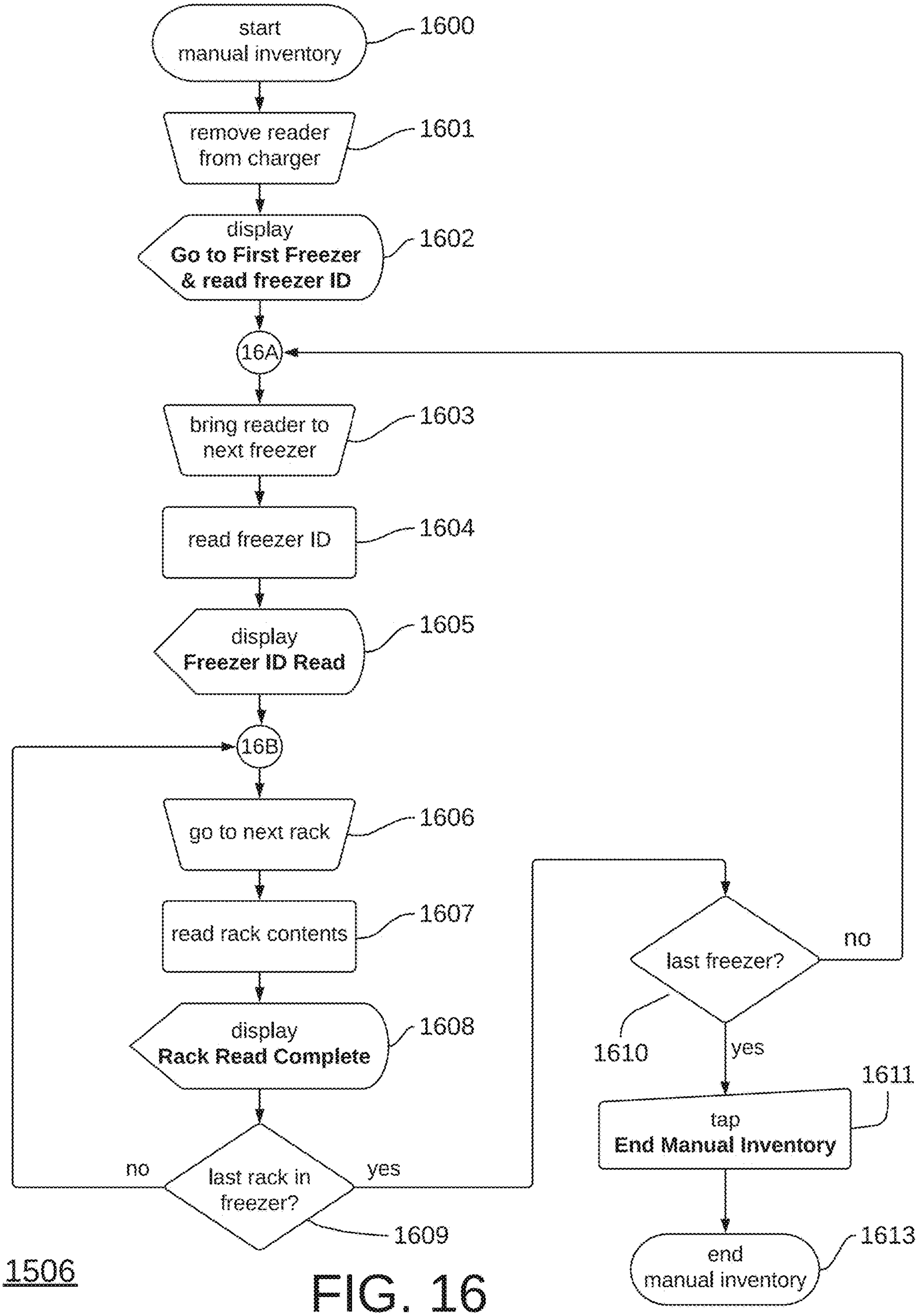
FIG. 16 is a flow diagram of the processing associated with the manual inventory process of FIG. 15.

FIG. 16 is a flow diagram of the processing associated with the manual inventory process 1506 of FIG. 15. The manual inventory process 1506 can be used to scan a freezer, rack, box, or sample that was previously unknown to the system controller. In an event such as this, the system controller will alert the user to the situation, and the system controller will add the object to the database as described in FIGS. 18-20 and 28.

The manual inventory process starts at step 1600. At step 1601, the user removes the handheld reader from its power charger (not shown). Depending on the particular system, the reader may be any of reader 800 of FIG. 8A, reader 840 of FIG. 8C, reader 1100 of FIG. 11, or any other suitable reader. At step 1602, the system controller displays the message "Go to first freezer & read freezer ID." At step 1603, the user brings the reader to a freezer; at step 1604, the user uses the reader to read the freezer ID; and, at step 1605, the system controller displays the message "Freezer ID read."

The database may be updated at the end of a particular routine or at multiple places in each routine. Exactly when during each process the database will be updated will depend on specific hardware and software implementations. As one example, if a handheld reader is used, the reader can be connected to the system at all times and database updates can be made whenever appropriate. But, if the handheld reader is not connected, the database update may happen only when the handheld reader is placed back in its charging/docking station. This applies to all of the routines in FIG. 15.

At step 1606, the user brings the reader to a rack of the current freezer; at step 1607, the user uses the reader to read the contents of the rack, e.g., as described previously in the context of FIGS. 8A, 9B, and 11; and, at step 1608, the system controller displays the message "Rack read complete."

If the user determines at step 1609 that the current rack is not the last rack in the current freezer, then processing returns to step 1606 to read another rack in the current freezer. Otherwise, processing continues to step 1610. If the user determines at step 1609 that the current freezer is not the last freezer in the system, then processing returns to step 1603 to inventory another freezer in the system. Otherwise, processing continues to step 1611, where the user selects "End Manual Inventory" on the system controller's display.

Figure 17:
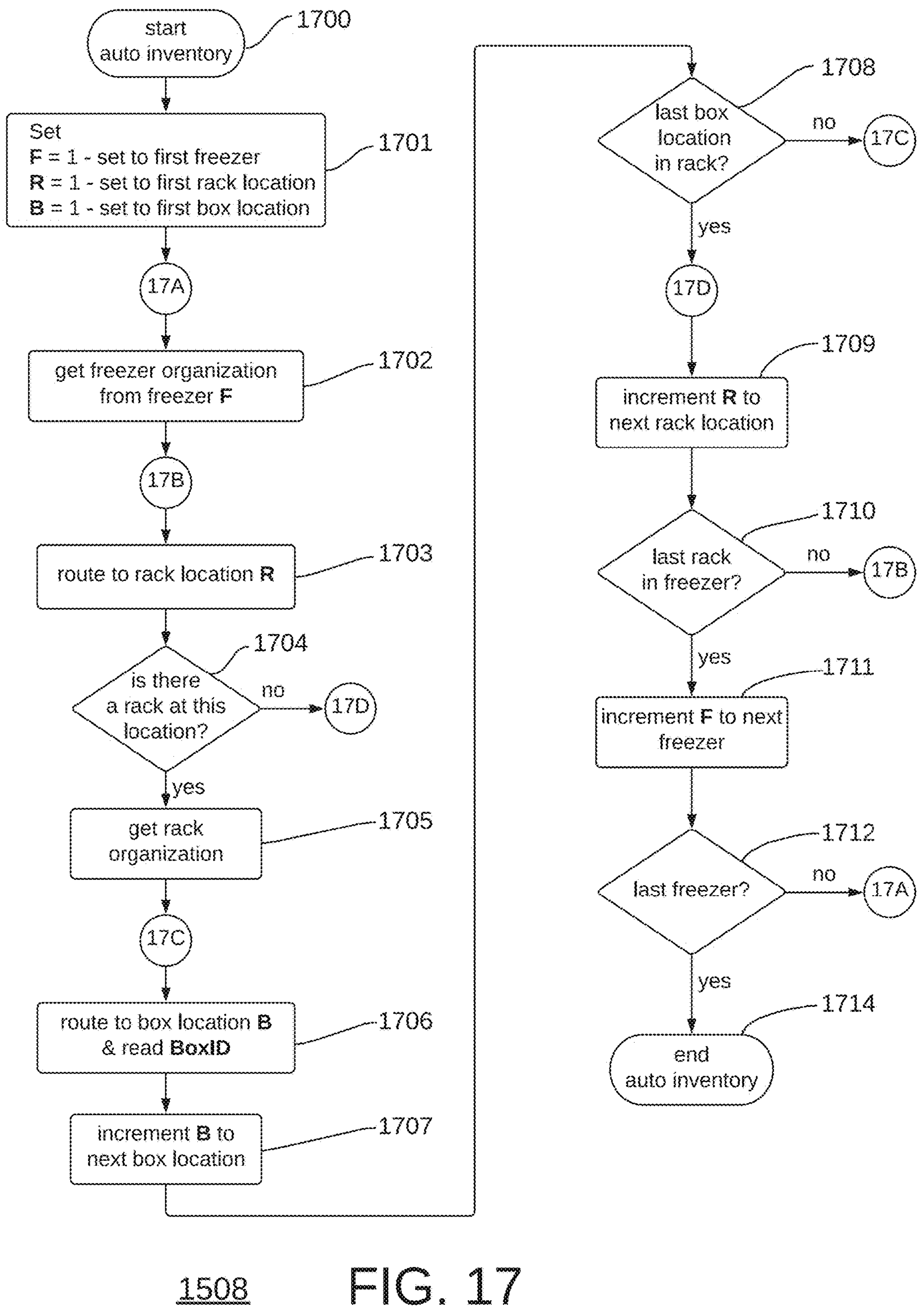
FIG. 17 is a flow diagram of the processing associated with the automatic inventory process of FIG. 15.

FIG. 17 is a flow diagram of the processing associated with the automatic inventory process 1507 of FIG. 15. The automatic inventory process 1507 can be used to accession a freezer, rack, box, or sample that was previously unknown to the system.

The automatic inventory process starts at step 1700. At step 1701, the system controller sets the location parameters F (for freezer ID), R (for rack ID), and B (for box ID) to (1:1:1) to indicate the location of the first box in the first rack of the first freezer in the system. Note that, in this implementation, the freezers do not have shelves. For freezers with shelves, the location signature would include an additional location parameter S (for shelf ID) between F and R.

At step 1702, the system controller queries freezer F and asks how many racks are in the freezer. The freezer replies with the number of racks.

At step 1703, the system controller routes to the rack location R. If the system controller determines, at step 1704, that there is no rack at rack location R of the current freezer F, for example, using the proximity sensors described earlier, then processing proceeds to step 1709. Otherwise, the system controller determines at step 1704 that a rack is at rack location R, and, at step 1705, the system controller gets the rack's organization (the number of boxes, for example).

At step 1706, the system controller connects to box location B in the current rack R of the current freezer F and, after confirming that there is a box at that location, the system controller reads the box's RFID, e.g., as described previously in the context of FIGS. 3, 4, 7, 8C, 10, and 12. At step 1707, the system controller increments the box location parameter B. If the system controller determines at step 1708 that the previous box was not the last box in the current rack R (e.g., because the box parameter B does not exceed the maximum number of boxes in rack R as stored in the system database or determined by the binary-coded rack code sensors, as described above), then the processing returns to step 1706 to read the box at location B in the current rack R of the current freezer F. Otherwise, processing continues to step 1709.

At step 1709, the system controller increments the rack location parameter R. If the system controller determines at step 1710 that the previous rack was not the last rack in the current freezer F (e.g., because the rack parameter R does not exceed the maximum number of racks in freezer F as stored in the system database), then the processing returns to step 1703 to process the rack at location R of the current freezer F. Otherwise, processing continues to step 1711.

At step 1711, the system controller increments the freezer location parameter F. If the system controller determines at step 1712 that the previous freezer was not the last freezer in the system (e.g., because the freezer parameter F does not exceed the maximum number of freezers in the system as stored in the system database), then the processing returns to step 1702 to process the freezer at location F in the system. Otherwise, processing continues to step 1714 where the automatic inventory process is terminated.

Figure 18:
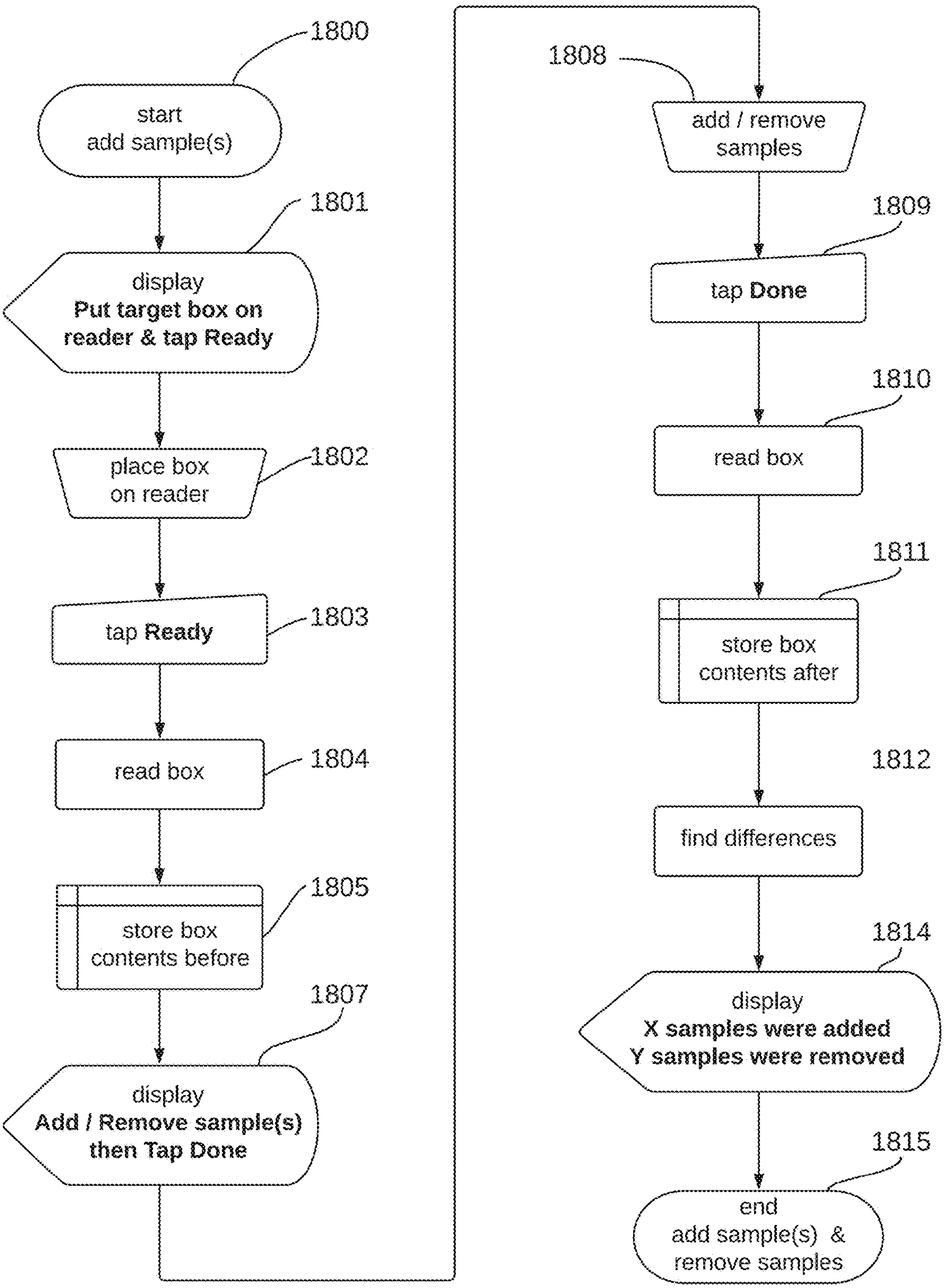
FIG. 18 is a flow diagram of the processing associated with the add sample process and the remove sample process of FIG. 15.

FIG. 18 is a flow diagram of the processing associated with the add sample process 1510 and the remove sample process 1514 of FIG. 15. This processing is used to add or remove one or more samples to or from a particular box. The add/remove sample process starts at step 1800. Note that, in some implementations, the user can add one or more samples and remove one or more other samples for the same box in a single process.

At step 1801, the system controller displays "Put target box on reader and tap 'Ready'." At step 1802, the user places the box on a box reader. In some implementations, the reader is a box mapper such as described in the cited patent matters. At step 1803, the user selects "Ready" on the system controller's display; at step 1804, the system controller controls the box reader to read the contents of the box (e.g., the RFIDs of the samples stored in the box identified by their locations within the box). In some embodiments the box reader will automatically read the box contents and selecting "Ready" will not be necessary.

At step 1807, the system controller displays "Add/Remove sample(s) then tap 'Ready'," and, at step 1808, the user adds or removes one or more samples to or from the box.

At step 1809, the user selects "Done"; at step 1810, the system controller controls the box reader to re-read the contents of the updated box; and, at step 1811, the system controller stores the updated box contents information in the system database. At step 1812, the system controller determines differences between the two sets of box contents information. At step 1814, the system controller displays, as appropriate, "X sample(s) was (were) added" and/or "X sample(s) was (were) removed," where X and Y are the number of samples that were added or removed, respectively; and, at step 1815, the process is terminated.

Figure 19:
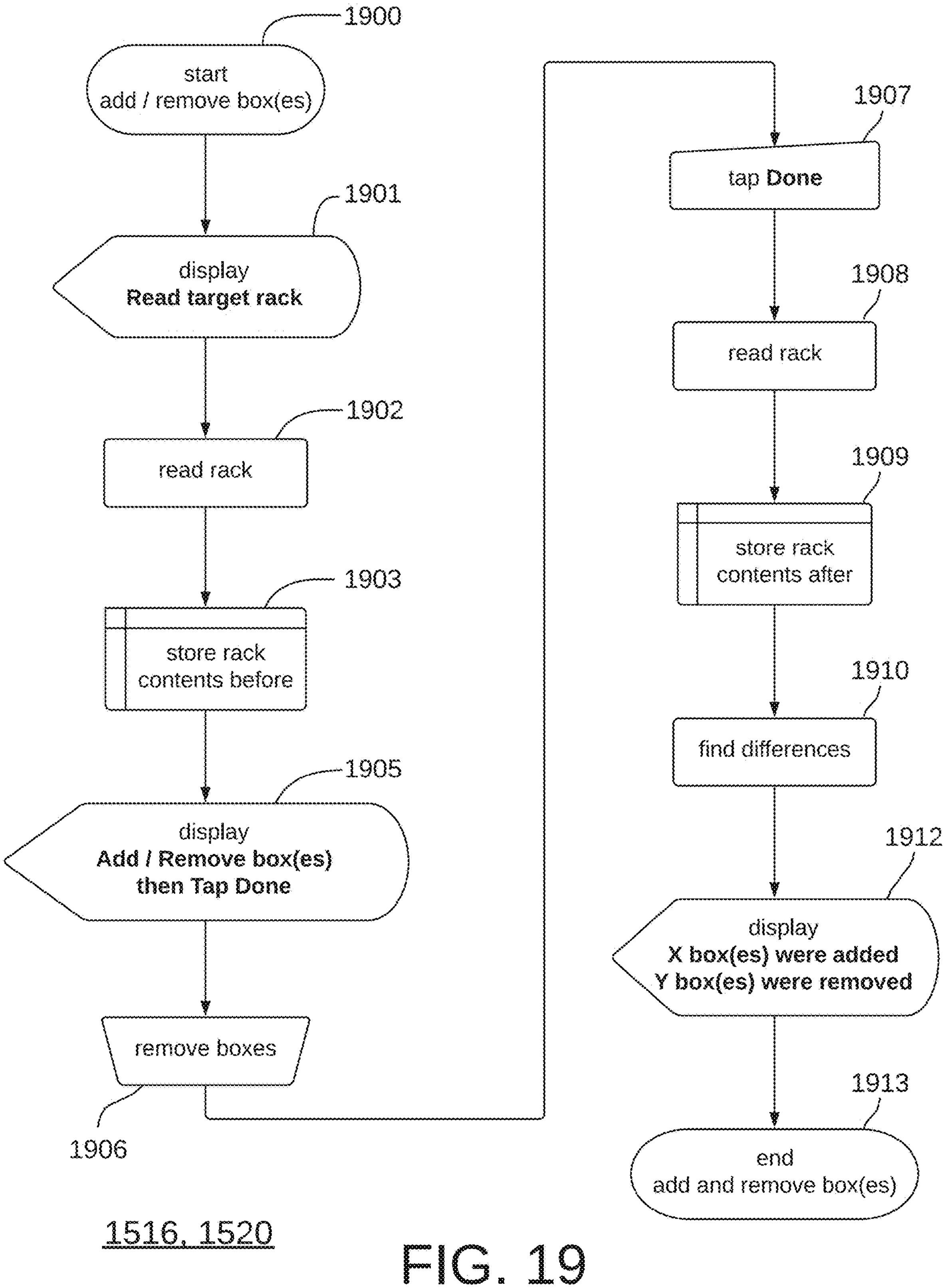
FIG. 19 is a flow diagram of the processing associated with the add box process and the remove box process of FIG. 15.

FIG. 19 is a flow diagram of the processing associated with the add box process 1516 and the remove box process 1520 of FIG. 15. This processing is used to add or remove one or more boxes to or from a particular rack. The add/remove box process starts at step 1900. Note that, in some implementations, the user can add one or more boxes and remove one or more other boxes for the same rack in a single process.

At step 1901, the system controller displays "Read target rack." At step 1902, the system controller determines the boxes that are currently in the rack and, at step 1903, the system controller stores the current rack contents information in the system database.

At step 1905, the system controller displays "Add/Remove box(es) then tap 'Done'," and, at step 1906, the user adds or removes one or more boxes to or from the rack.

At step 1907, the user selects "Done"; at step 1908, the system controller re-read the contents of the updated rack; and, at step 1909, the system controller stores the updated rack contents information in the system database. At step 1910, the system controller determines differences between the two sets of rack contents information; at step 1912, the system controller displays, as appropriate, "X box(es) was (were) added" and or "Y box(es) was (were) removed," where X and Y are the number of boxes that were added or removed, respectively.

Figure 20:
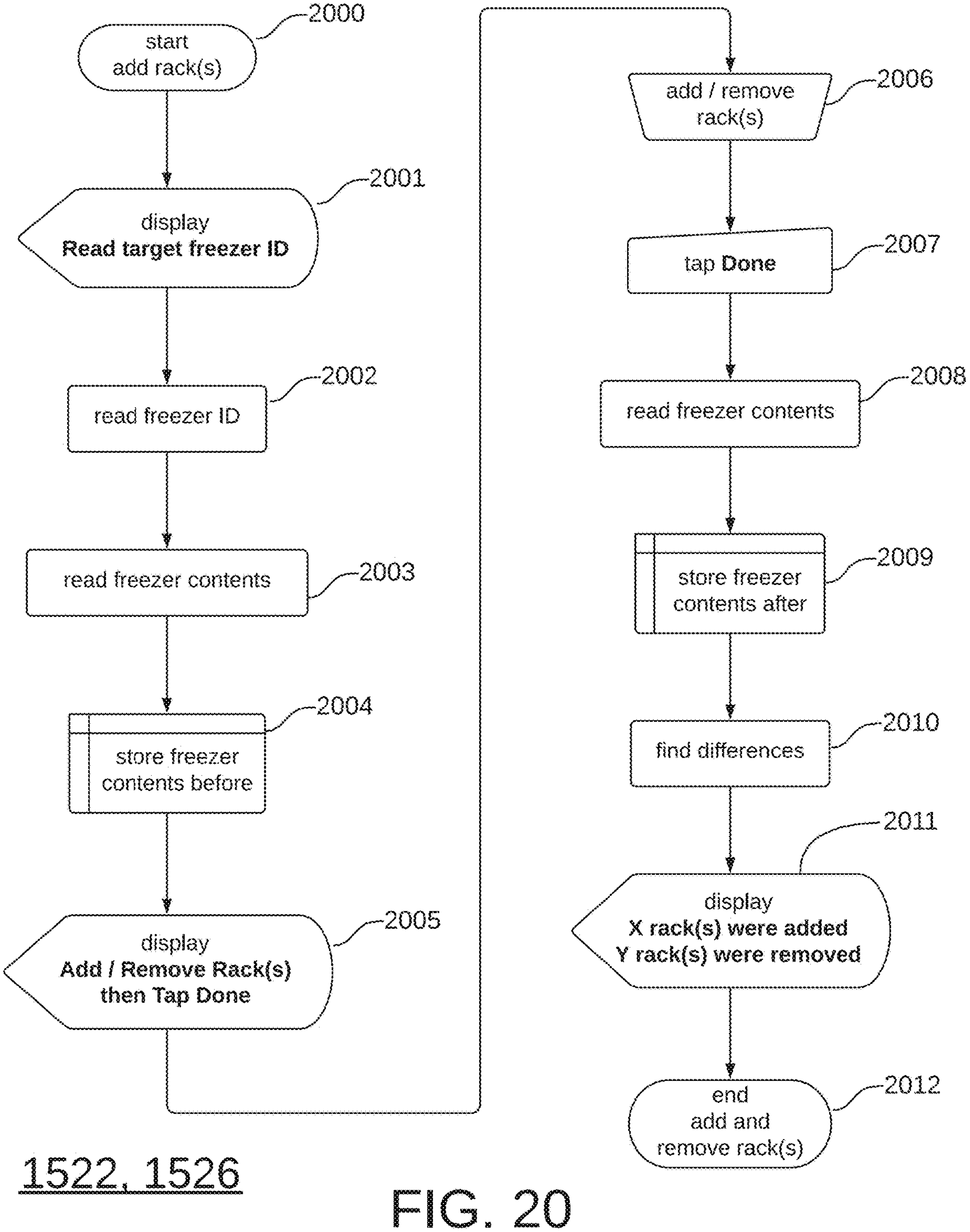
FIG. 20 is a flow diagram of the processing associated with the add rack process and the remove rack process of FIG. 15.

FIG. 20 is a flow diagram of the processing associated with the add rack process 1522 and the remove rack process 1526 of FIG. 15. This processing is used to add or remove one or more racks to or from a particular freezer. The add/remove rack process starts at step 2000. Note that, in some implementations, the user can add one or more racks and remove one or more other racks for the same freezer in a single process.

At step 2001, the system controller displays "Read target freezer ID," and at step 2002, the system controller reads the freezer ID.

At step 2004, the contents of the freezer is stored.

At step 2005, the system controller displays "Add/Remove Rack(s) then tap "Done."

At step 2006, the user adds or removes racks. Once the rack addition/removal is complete, the user taps "Done" at step 2007. Once again, the freezer contents is read (2008) and stored (2009). At step 2010, the differences between the before and after rack inventory is determined and displayed at step 2011. Step 2012 ends this process.

Figure 21:
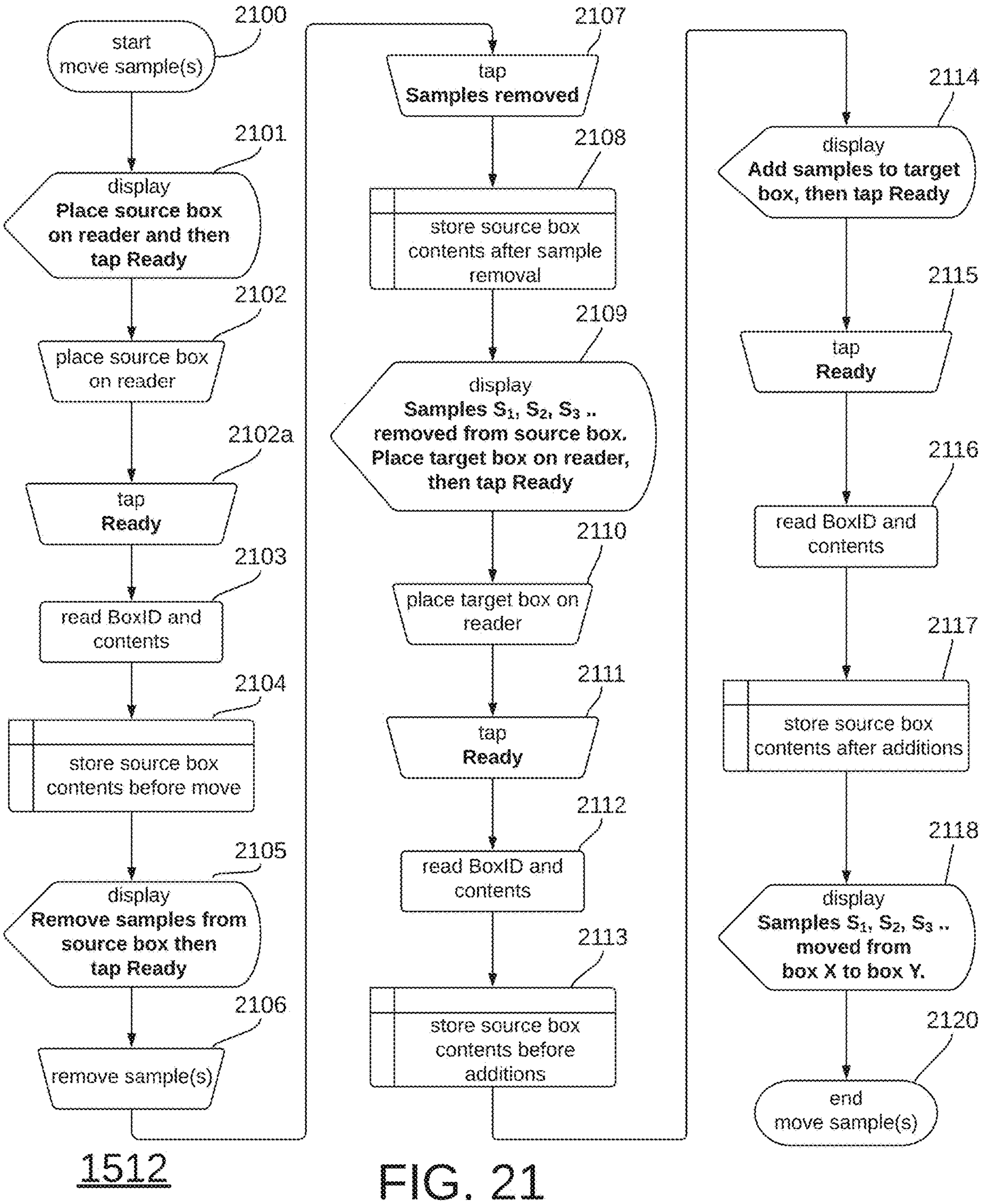
FIG. 21 is a flow diagram of the processing associated with the move sample process of FIG. 15.

FIG. 21 is a flow diagram of the processing associated with the move sample process 1512 of FIG. 15. This processing is used to move one or more samples from a source box to a different, target box. The move sample process starts at step 2100.

At step 2101, the system controller displays "Place source box on reader"; at step 2102, the user places the source box on the box reader (e.g., a box mapper) and taps "Ready" at step 2102a. At step 2103, the system controller controls the box reader to read the source box RFID and the contents of the source box; and, at step 2104, the system controller stores the source box RFID and the source box contents information in the system database.

In certain implementations, the system controller might indicate to the user to tap "Ready" after placing boxes on the reader but, in other implementations, the reader identifies the box placement automatically, for example, by reading the box RFID tag. This applies here and to all places where the user taps "Done" or "Ready" when a box is ready to be read by the box reader.

At step 2105, the system controller displays "Remove samples from source box then tap 'Samples Removed'," and, at step 2106, the user removes one or more samples from the source box. As step 2107, the user selects "Samples Removed" on the system controller's display and, at step 2108, the system controller controls the box reader to re-read the contents of the source box and stores the updated source box contents information in the system database.

At step 2109, the system controller displays, as appropriate, "Samples $S_1, S_2, S_3, \ldots$ removed from source box. Place target box on reader, then select 'Ready'," where $S_i$ is the ID of the $l^{th}$ sample; at step 2110, the user places the target box on the box reader; at step 2111, the user selects "Ready" on the system controller's display; at step 2112, the system controller controls the box reader to read the target box RFID and the contents of the target box; and, at step 2113 the system controller stores the target box RFID and the target box contents information in the system database.

At step 2114, the system controller displays "Add samples to target box then tap "Ready" and, at step 2115, the user adds to the source box the one or more samples that were removed from the target box and selects "Ready" on the system controller's display. At step 2116, the system controller controls the box reader to re-read the contents of the target box; and, at step 2117 the system controller stores the target box RFID and the target box contents information in the system database.

At step 2118, the system controller displays, as appropriate, "Samples $S_1, S_2, S_3, \ldots$ moved from source box B to target box B". At step 2120, the process is terminated.

In a fully automatic system, moving boxes between racks can be done by moving boxes between racks as needed. Once the source and target racks are in the freezer, an automatic inventory can be performed, and the box locations will be updated. Here, a scenario is described where a specific box(es) need to be moved between specific racks, for shipping purposes, for example. In this case, the rack reader is similar to those shown in FIGS. 8 and 11.

Figure 22:
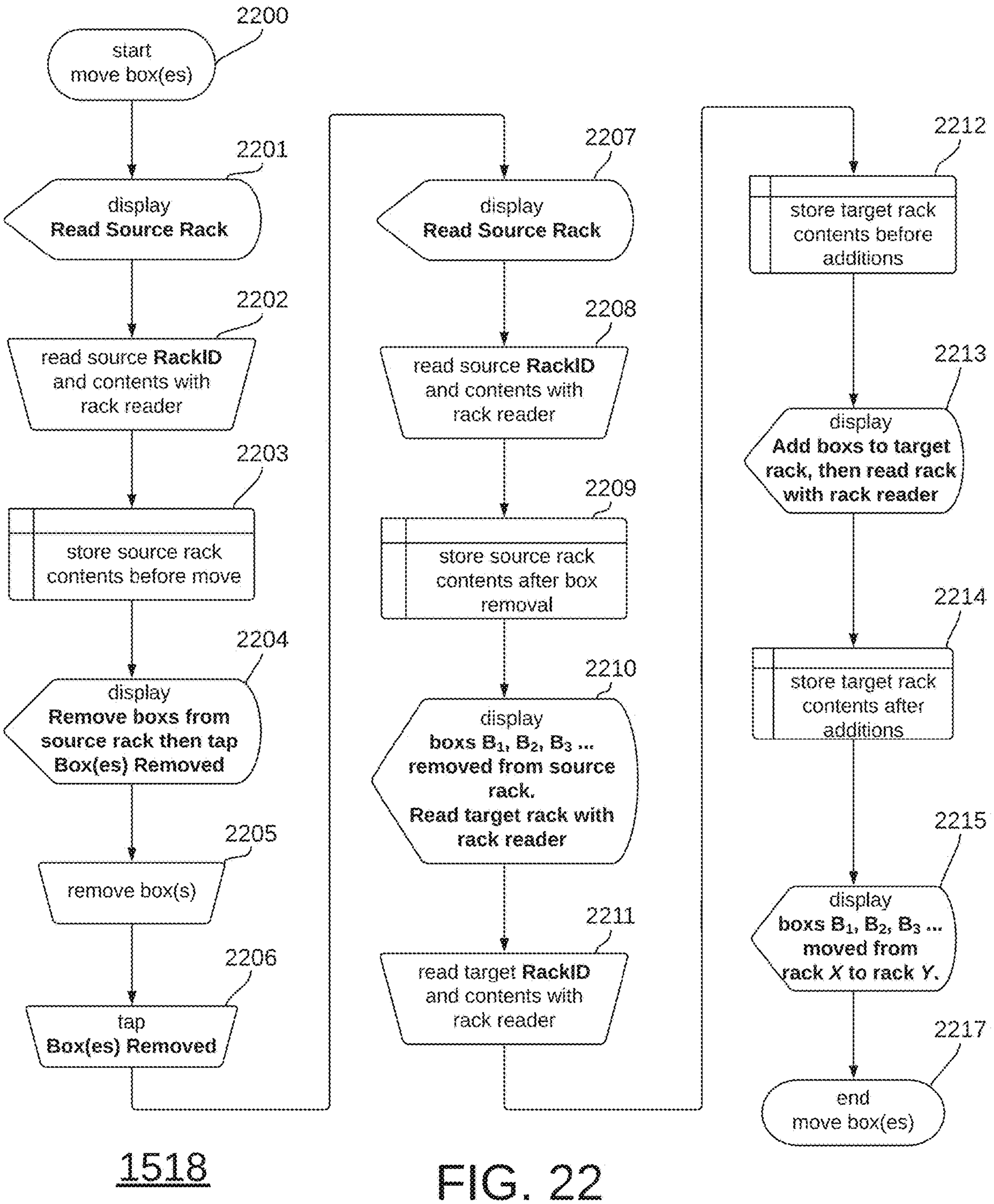
FIG. 22 is a flow diagram of the processing associated with the move box process of FIG. 15.

FIG. 22 is a flow diagram of the processing associated with the move box process 1518 of FIG. 15. This processing is used to move one or more boxes from a source rack to a different, target rack. The move box process starts at step 2200.

At step 2201, the system controller displays "Read source rack"; at step 2202, the system controller reads the source rack RFID and the contents of the source rack with the rack reader; and, at step 2203, the system controller stores the source rack RFID and the source rack contents information in the system database.

At step 2204, the system controller displays "Remove box(es) from source rack then tap 'Box(es) Removed'," and, at step 2205, the user removes one or more boxes from the source rack. As step 2206, the user selects "Box(es) Removed" on the system controller's display; at step 2207, the system controller displays "Read source rack"; at step 2208, the system controller re-reads the contents of the source rack; and, at step 2209, the system controller stores the updated source rack contents information in the system database.

At step 2210, the system controller displays, as appropriate, "Box(es) $B_1, B_2, B_3, \ldots$ removed from source rack. Read target rack with rack reader," where $B_i$ is the ID of the $l^{th}$ box; at step 2211, the system controller reads the target rack RFID and the target rack contents with the rack reader and, at step 2212, the system controller stores the target rack RFID and the target rack contents information in the system database.

At step 2213, the system controller displays "Add boxes to target rack, then read rack with rack reader," and, at step 2214, the user adds to the target rack the boxes that were removed from the source rack, the system controller re-reads the target rack contents with the rack reader and stores the updated target rack contents information in the system database.

At step 2215, the system controller displays, as appropriate, "Box(es) $B_1, B_2, B_3, \ldots$ moved from rack X to rack Y", and, at step 2217, the process is terminated.

In a fully automatic system, moving racks between freezers can be done by simply moving the racks between freezers as needed. Once the move has taken place, an automatic inventory can be initiated and the rack and box locations will be updated. Here a scenario is described where specific racks need to be moved between specific freezers, for shipping purposes, for example. In this case, the rack reader is similar to those shown in FIGS. 8 and 11.

Figure 23:
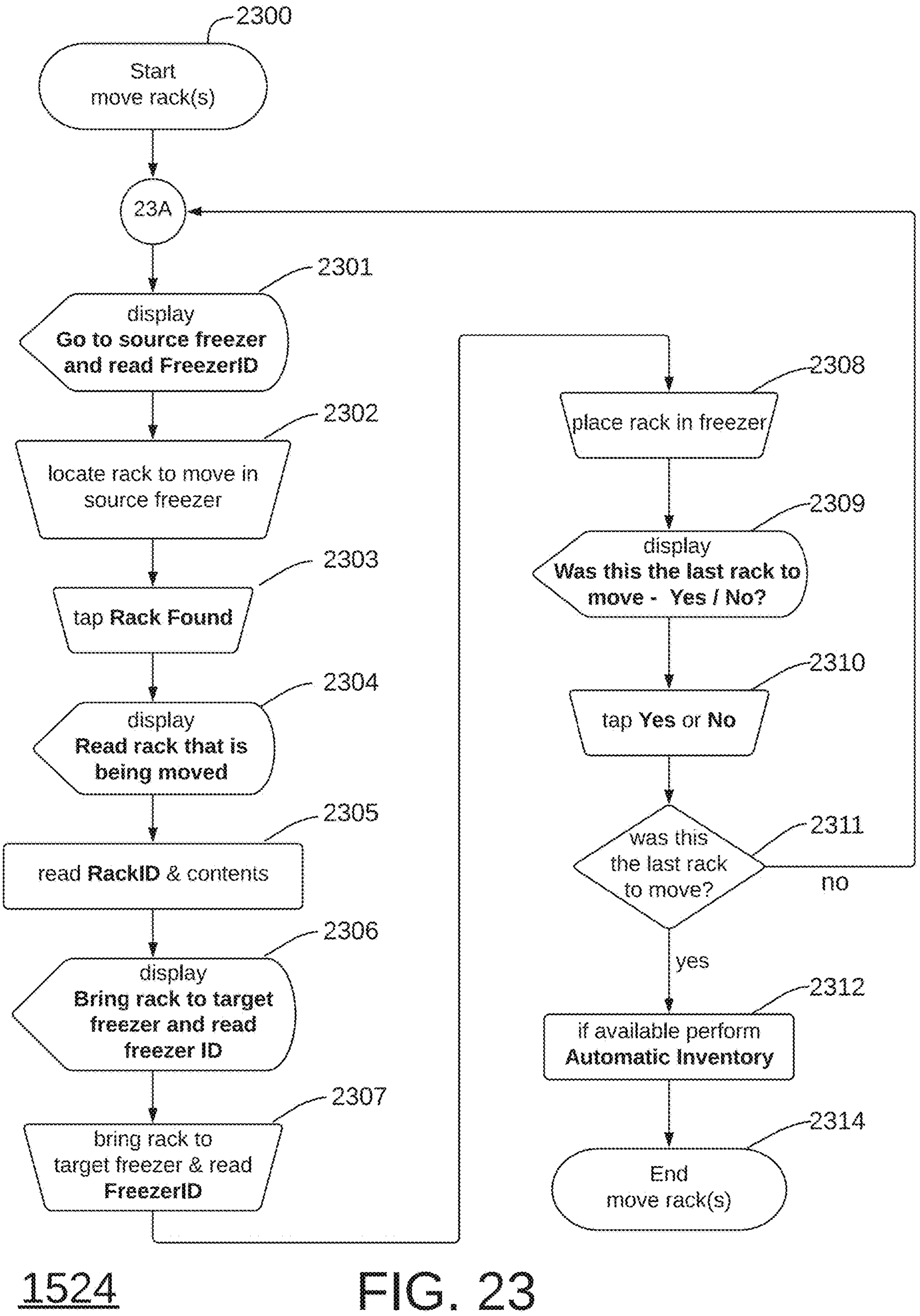
FIG. 23 is a flow diagram of the processing associated with the move rack process of FIG. 15.

FIG. 23 is a flow diagram of the processing associated with the move rack process 1524 of FIG. 15. This processing is used to move one or more racks from a source freezer to a different, target freezer. The move rack process starts at step 2300.

At step 2301, the system controller displays "Go to source freezer and read FreezerID"; at step 2302, the user goes to the source freezer, uses a handheld reader to read the freezer RFID as described in FIG. 9, and locates a rack to be moved. At step 2303, the user selects "Rack Found" on the system controller's display and, at step 2304, the system controller displays "Read rack that is being moved." At step 2305, the user uses the handheld reader to read the rack RFID and the contents of the rack.

At step 2306, the system controller displays "Bring rack to target freezer and read freezer ID." At step 2307, the user brings to the target freezer the rack that was removed from the source freezer and uses the handheld reader to read the target freezer RFID. At step 2308, the user places the rack into the target freezer.

At step 2309, the system controller displays "Was this the last rack to move—Yes/No?" At step 2310, the user selects either "Yes" or "No" on the system controller's display. If the system controller determines at step 2311 that the previous rack was not the last rack to move, then processing returns to step 2301 to move another rack from the same or different source freezer to the same or different target freezer. Otherwise, processing continues to step 2312.

At step 2312, if available, the system controller can perform an automatic inventory process 1508 of FIGS. 15 and 17 on the source freezer and/or the target freezer and, at step 2314, the process is terminated.

Figure 24:
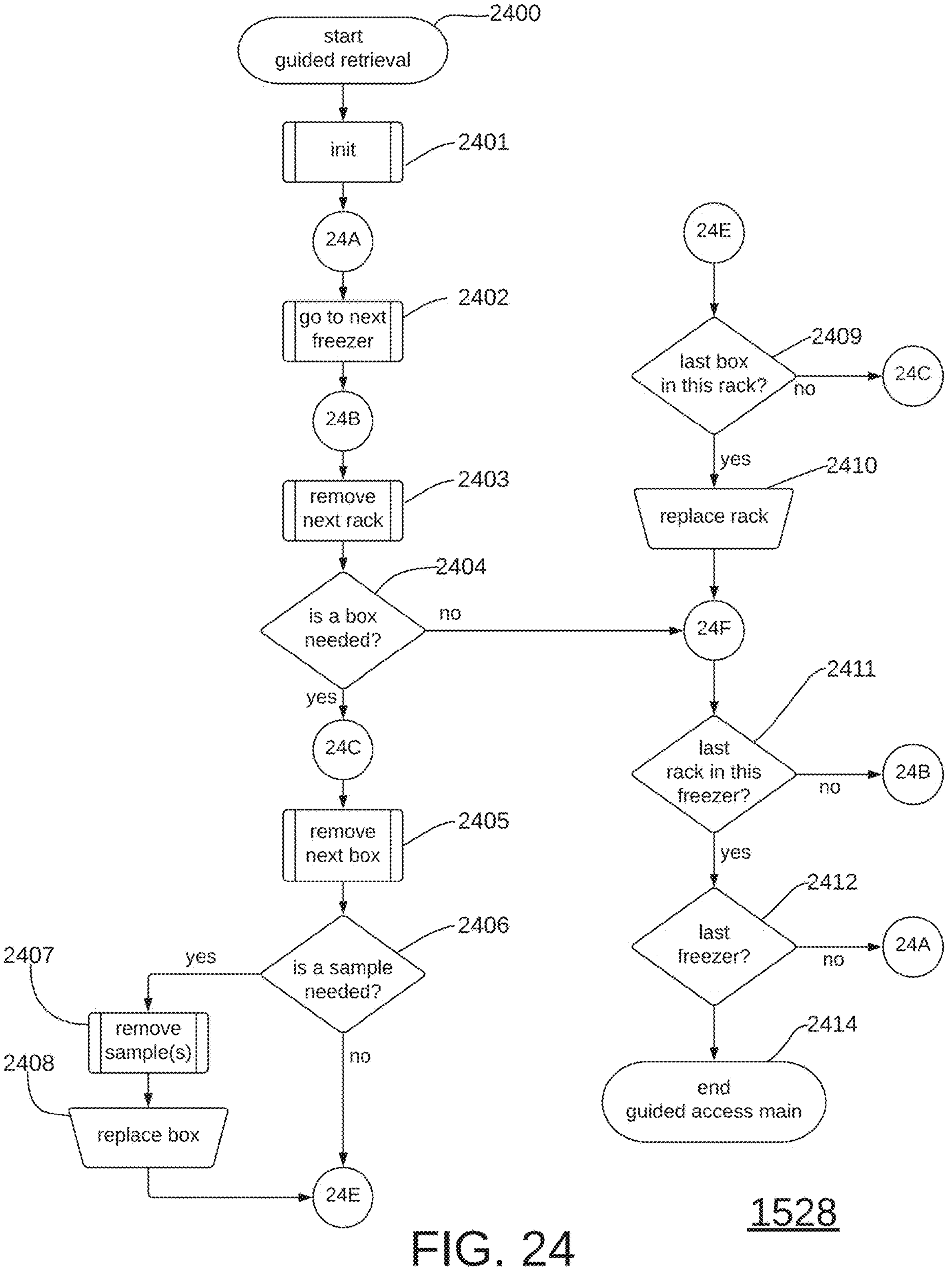
FIG. 24 is a flow diagram of the processing associated with the guided retrieval process of FIG. 15.

FIG. 24 is a flow diagram of the processing associated with the guided retrieval process 1528 of FIG. 15. This processing is used to remove one or more samples from one or more freezers using the guided retrieval technique described in the cited patent matters. As described in the cited patent matters, the guided retrieval technique can take into account one or more of the following criteria: a) minimizing freezer door open time, b) minimizing number of door openings, c) minimizing rack time out of freezer, d) minimizing sample time out of freezer, e) minimizing overall pick time, and f) limiting the number of samples that can be handled at a time. The guided retrieval process starts at step 2400.

Figure 25:
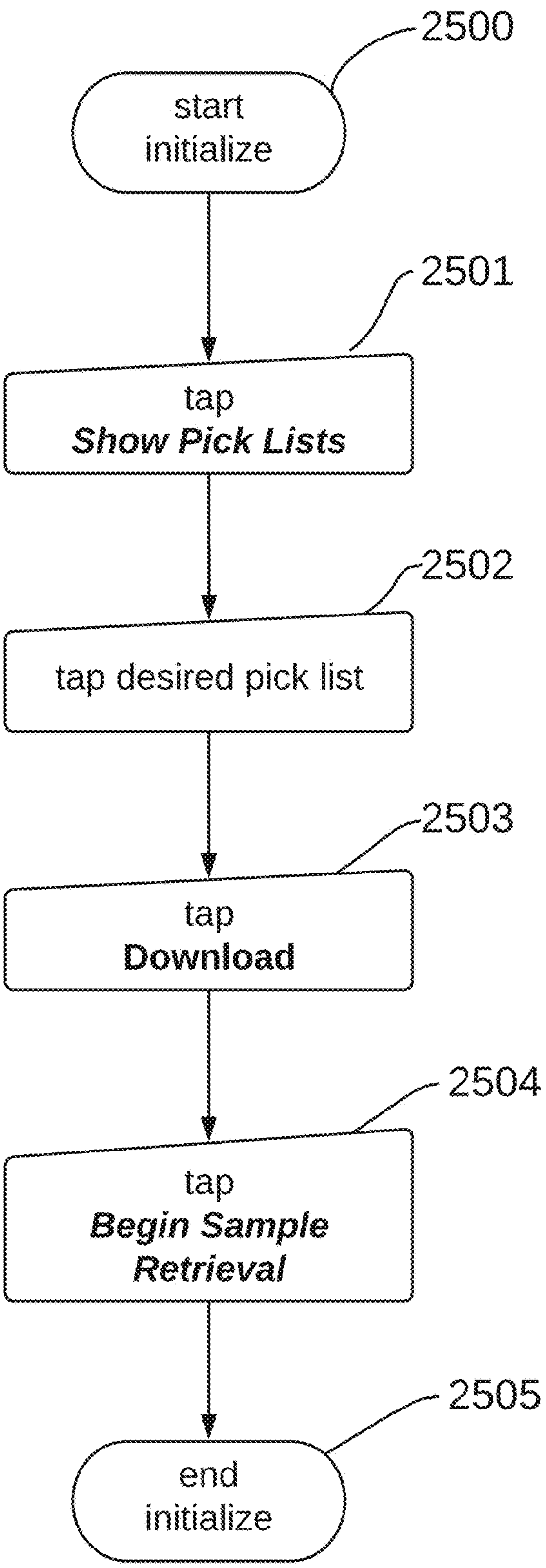
FIG. 25 is a flow diagram of the processing associated with the initialization step of FIG. 24.

At step 2401, the system controller initializes the guided retrieval process as described more fully with reference to FIG. 25. In particular, the initialization step starts at step 2500 of FIG. 25. A pick list is a list of one or more samples to be removed from the system. At step 2501, the user selects "Show Pick Lists" on the system controller's display. The system controller sends a list of pick lists to the user. There might be only one pick list or there might be several depending on the implementation of the system. For example, if the user is in building A, he might choose only pick lists of samples that are in building A and ignore for the time being samples that are located in other buildings. At step 2502, the user selects a desired pick list by tapping on it. At step 2503, the user selects "Download" on the system controller's display, and the system controller downloads, from the system database, the location information for the samples on the chosen pick list. At step 2504, the user selects "Begin Sample Retrieval" on the system controller's display and, at step 2505, the initialization step is terminated.

Figure 26:
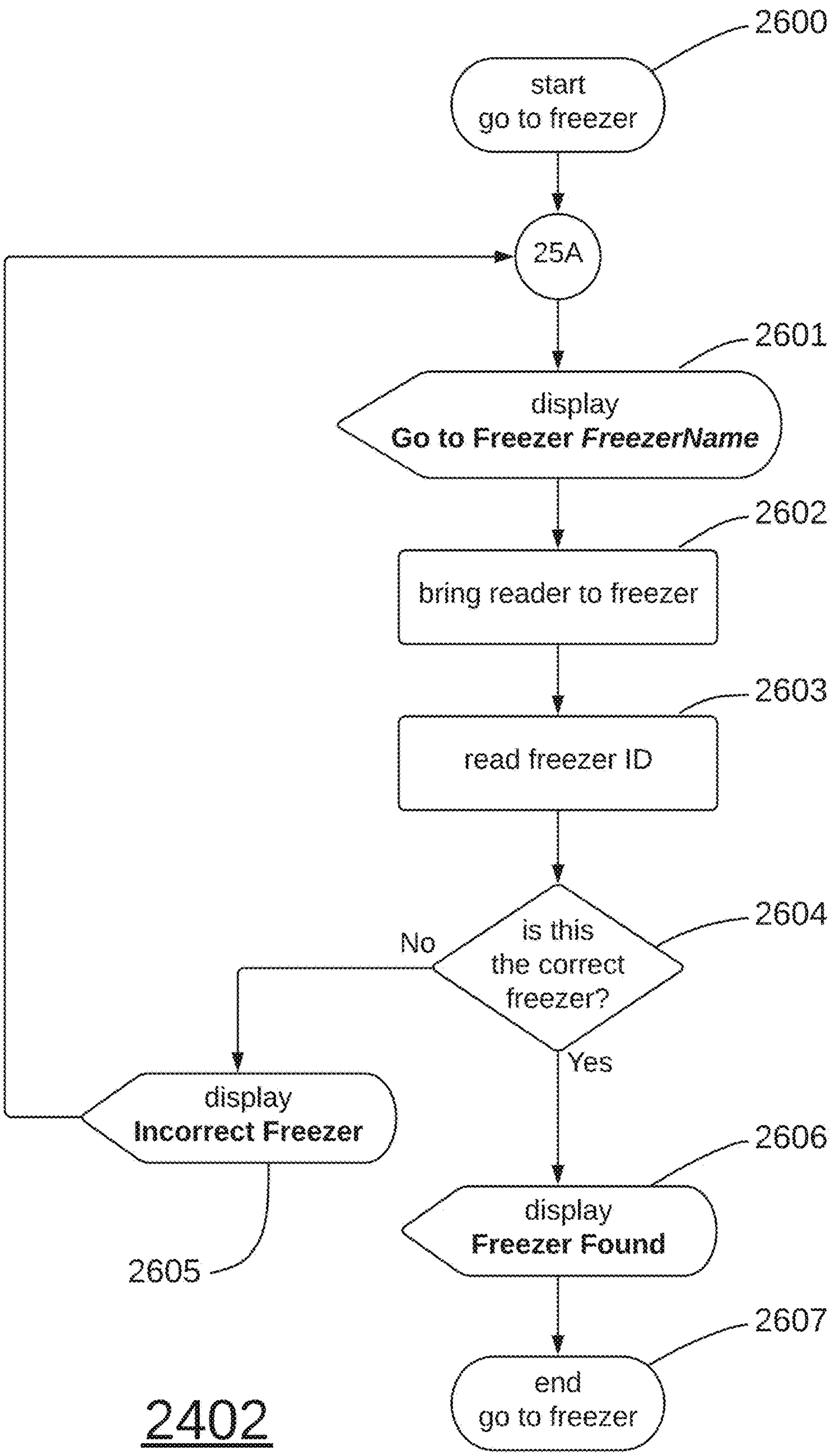
FIG. 26 is a flow diagram of the processing associated with the "go to freezer" step of FIG. 24.

Referring again to FIG. 24, at step 2402, the user goes to a freezer as described more fully with reference to FIG. 26. In particular, the "go to freezer" step 2402 starts at step 2600 of FIG. 26. At step 2601, the system controller displays "Go to freezer FreezerName," where FreezerName is a unique name for the current freezer. At step 2602, the system controller identifies the current freezer to the user, e.g., by illuminating a light on the freezer, and the user brings a handheld reader to the current freezer and, at step 2603, the user uses the handheld reader to read the freezer RFID of the current freezer. If the system controller determines at step 3604 that the user selected the wrong freezer, then, at step 2605, the system controller displays "Incorrect freezer" and processing returns to step 2601 to enable the user to select the correct freezer. Otherwise, at step 2606, the system controller displays "Freezer found" and, at step 2607, the "go to freezer" step is terminated.

Figure 27:
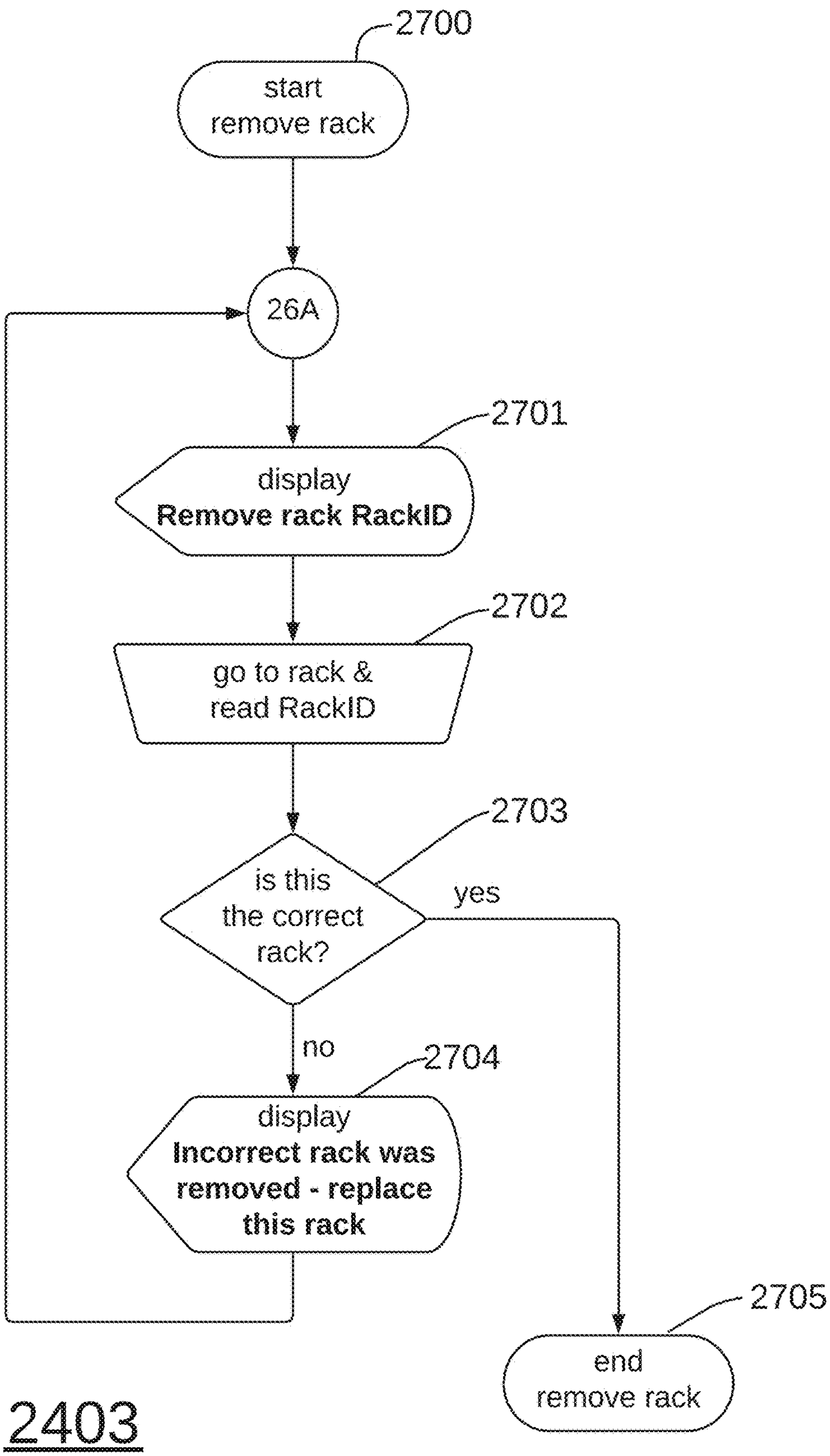
FIG. 27 is a flow diagram of the processing associated with the "remove rack" step of FIG. 24.

Referring again to FIG. 24, at step 2403, the user removes a rack from the current freezer as described more fully with reference to FIG. 27. In particular, the "remove rack" step 2403 starts at step 2700 of FIG. 27. At step 2701, the system controller displays "Remove rack RackID," where RackID is the rack RFID. At step 2702, the system controller identifies the current rack to the user, e.g., by illuminating a light on the rack, and the user uses the handheld reader to read the rack RFID of the current rack. If the system controller determines at step 2703 that the user selected the wrong rack, then, at step 2704, the system controller displays "Incorrect rack was removed—replace this rack" and processing returns to step 2701 to enable the user to replace the wrong rack and select the correct rack. Otherwise, at step 2705, the "remove rack" step is terminated.

Referring again to FIG. 24, if, at step 2404, the system controller determines that a box in the current rack is not needed, then processing proceeds to step 2411. Otherwise, a box is needed and processing continues to step 2405.

Figure 28:
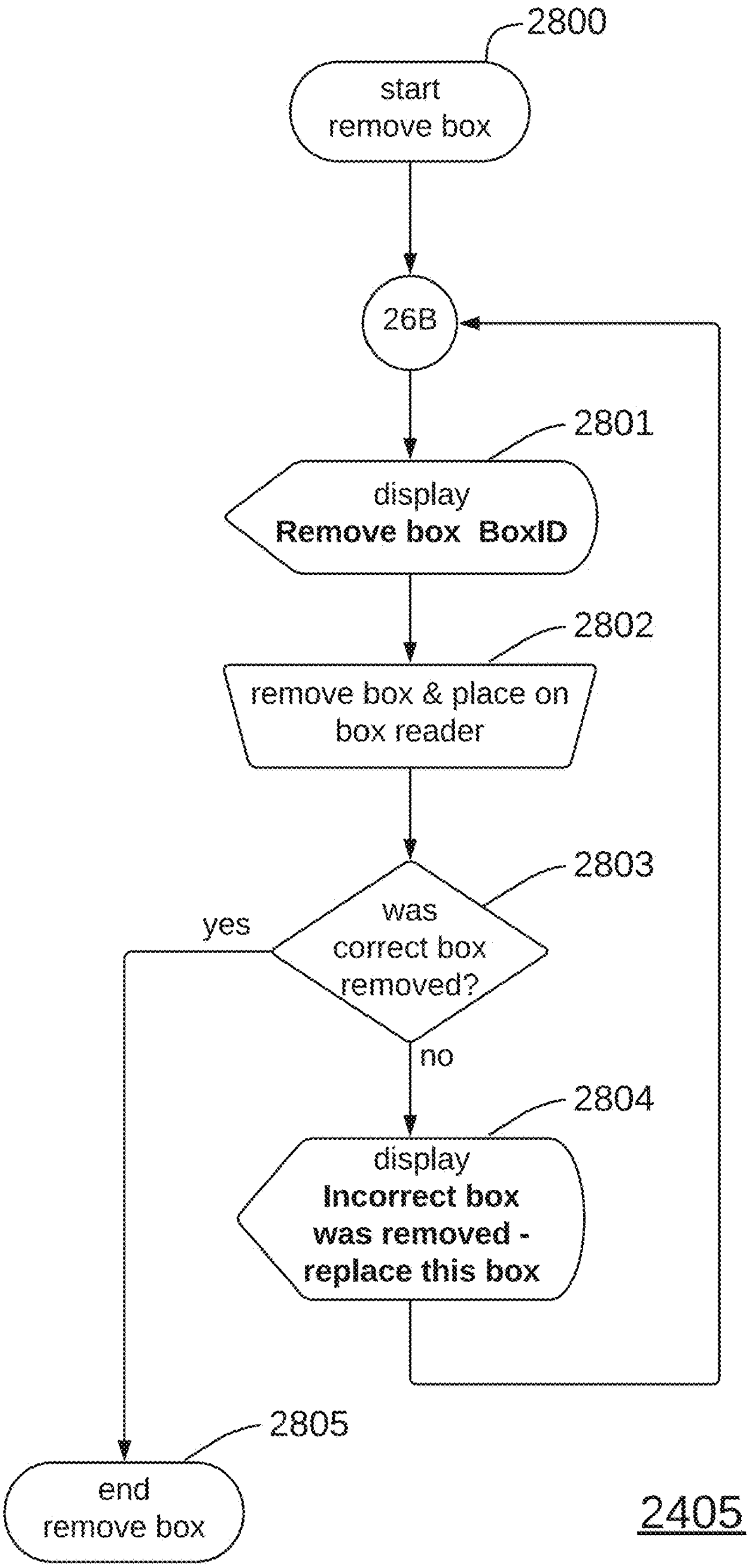
FIG. 28 is a flow diagram of the processing associated with the "remove next box" step of FIG. 24.

At step 2405, the user removes a box from the current rack as described more fully with reference to FIG. 28. In particular, the "remove next box" step 2405 starts at step 2800 of FIG. 28. At step 2801, the system controller displays "Remove box BoxID," where BoxID identifies the box to be removed from the current rack. At step 2802, the system controller indicates the box to be removed, e.g., by illuminating a light on the box, and the user removes the box and places it on a box reader. Note that the system controller controls the box reader to read the box RFID. If the system controller determines, at step 2803, that the wrong box was removed, then, at step 2804, the system controller displays "Incorrect box was removed—replace this box" and processing returns to step 2801 to enable the user to replace the wrong box and remove the correct box. Otherwise, the correct box was removed and, at step 2805, the "remove next box" step is terminated.

Referring again to FIG. 24, if the system controller determines at step 2406 that a sample is not needed, then processing continues to step 2409. Otherwise, processing continues to step 2407.

Figure 29:
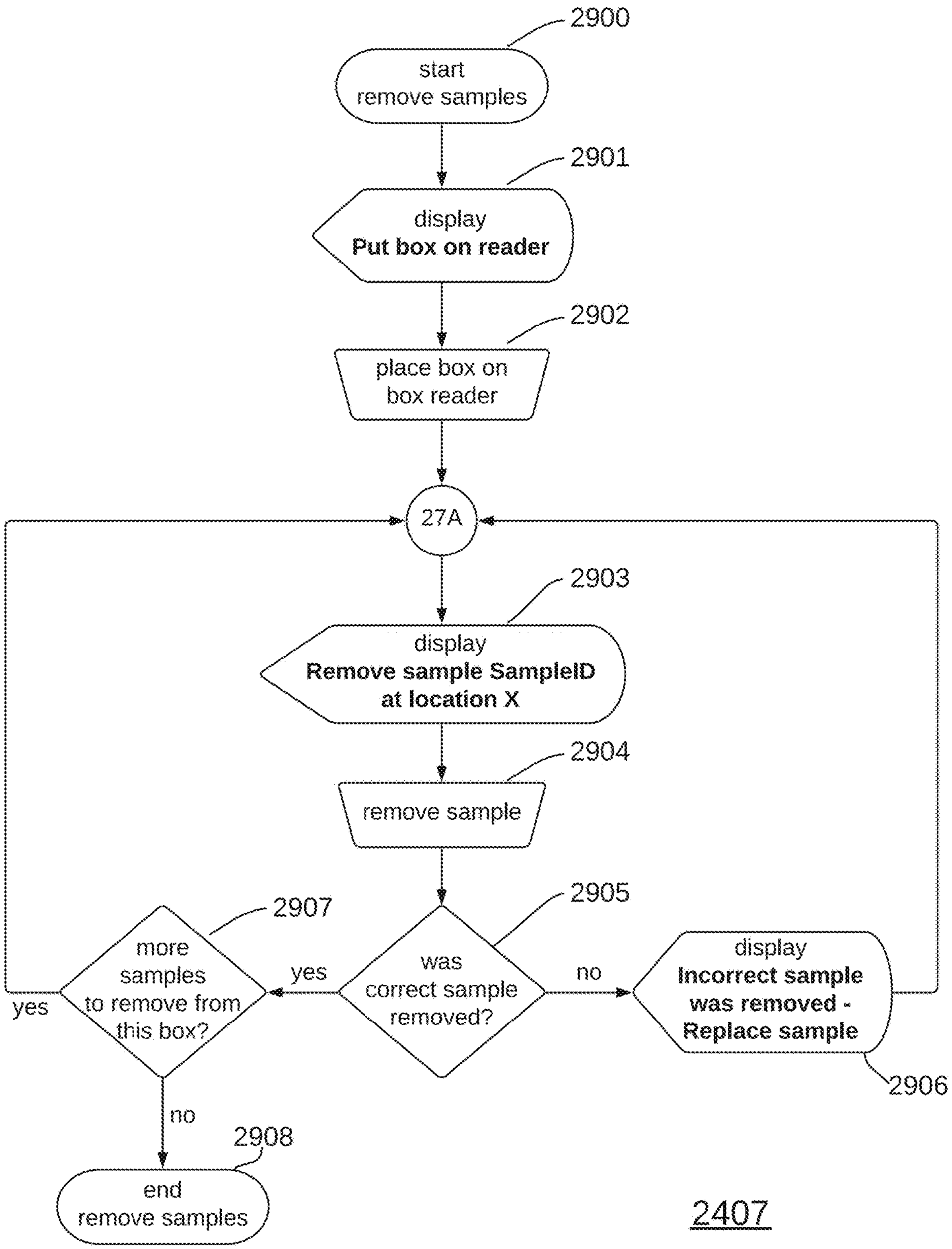
FIG. 29 is a flow diagram of the processing associated with the "remove samples" step of FIG. 24.

At step 2407, the user removes one or more samples from the current box as described more fully with reference to FIG. 29. In particular, the "remove samples" step 2407 starts at step 2900 of FIG. 29. At step 2901, the system controller displays "Put box on box reader." At step 2902, the user places the box on a box reader. Note that the system controller controls the box reader to read the contents of the box. At step 2903, the system controller displays "Remove sample SampleID at location X," where SampleID identifies the sample and X identifies a location within the box. At step 2904, the user removes the sample from the box, while the box is still on the box reader. As such, the system controller can control the box reader to detect the removal of the sample. If the system controller determines, at step 2905, that the wrong sample was removed, then, at step 2906, the system controller displays "Incorrect sample was removed—replace sample" and processing returns to step 2903 to enable the user to replace the wrong sample and remove the correct sample. Otherwise, the correct sample was removed and processing continues to step 2907. If the system controller determines, at step 2907, that at least one more sample is to be removed from the box, then processing returns to step 2903 to enable the user to remove another sample from the box. Otherwise, processing proceeds to step 2909, where the "remove samples" step is terminated.

Referring again to FIG. 24, at step 2408, the user returns the box to its rack. If the system controller determines at step 2409, that there is at least one more box in the current rack to process, then processing returns to step 2405 to remove the next box from the current rack. Otherwise, processing proceeds to step 2410, wherein the user returns the current rack to its freezer. If the system controller determines at step 2411, that there is at least one more rack in the current freezer to process, then processing returns to step 2403 to remove the next rack from the current freezer. Otherwise, processing proceeds to step 2412. If the system controller determines at step 2412, that there is at least one more freezer in the system to process, then processing returns to step 2402 to process the next freezer. Otherwise, at step 2414, the "guided retrieval" process is terminated.

Figure 30:
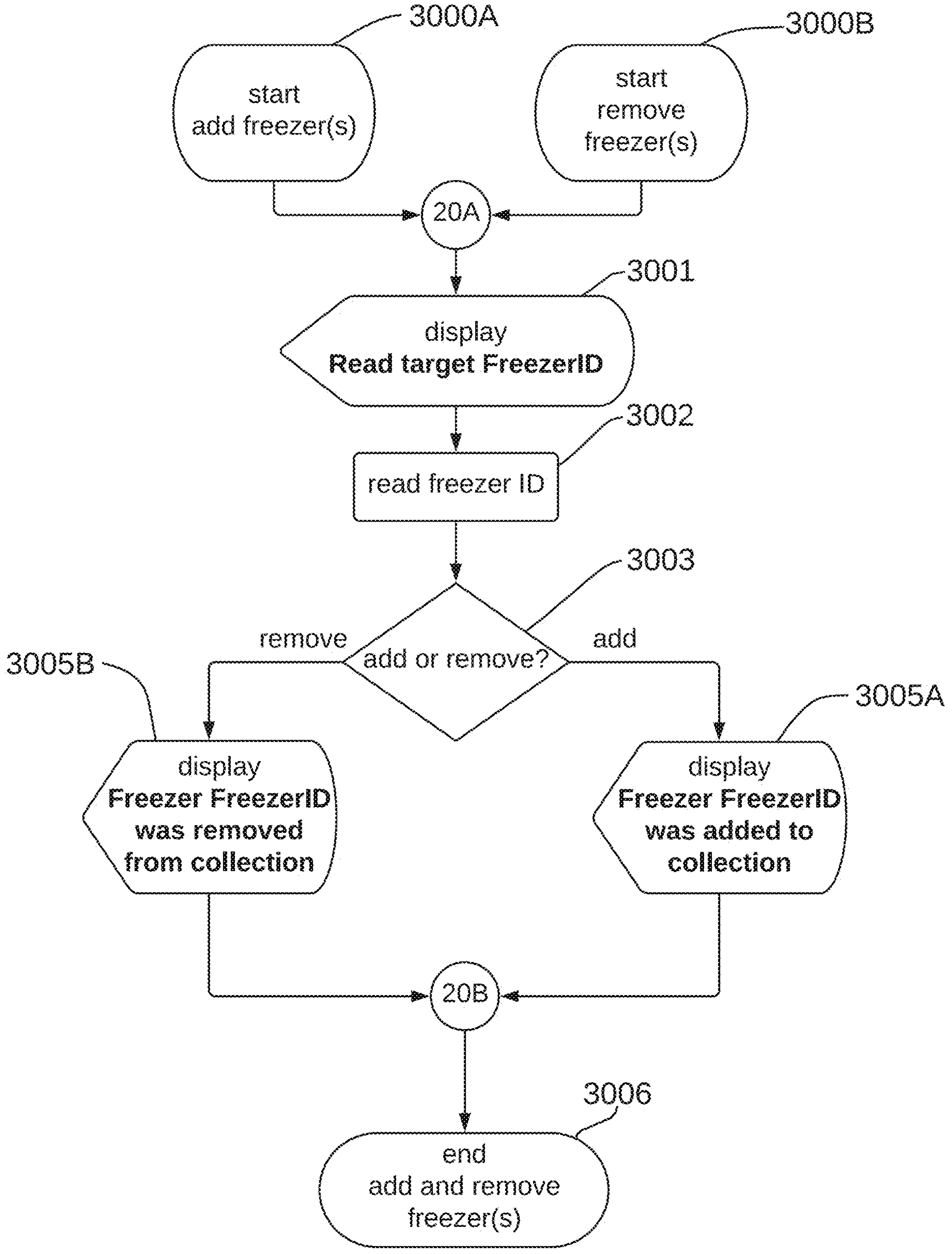
FIG. 30 is a flow diagram of the processing to add or remove a freezer to or from a cold-storage system.

FIG. 30 is a flow diagram of the processing to add or remove a freezer to or from a cold-storage system. The add freezer process starts at step 3000A, while the remove freezer process starts at step 3000B. Note that, in some implementations, the user can add one or more freezers and remove one or more other freezers for the same system in a single process.

At step 3001, the system controller displays "Read target FreezerID," where FreezerID identifies the freezer to be added or removed. At step 3002, the user uses a handheld reader to read the freezer RFID. If the process is the add freezer process (step 3003), then, at step 3004A, the system controller updates the system database to add the new freezer and, at step 3005A, the system controller displays "Freezer FreezerID was added to collection." Otherwise, at step 3004B, the system controller updates the system display to remove the freezer and, at step 3005B, the system controller displays "Freezer FreezerID was added to collection." At step 3006, the process is terminated.

Although the invention has been described in the context of cold-storage systems having freezers or dewars and cooled handling containers, those skilled in the art will understand that the invention can be implemented in other suitable contexts, including (without limitation) storage systems having other types of outer containers for storing samples at other than cold temperatures.

Although the invention has been described in the context of using RFID tags to identify various elements in the storage system, in other implementations, other types of wireless identification tags can be used such as (without limitation) near-field communications (NFC) tags or Bluetooth or Zigbee transceivers.

The invention has been described in the context of storage systems having various hierarchies containing boxes and racks and something shelves. Those skilled in the art will understand that other hierarchies are also possible. In certain embodiments having boxes of samples inside racks, a storage system has reader electronics that are (i) external to and distinct from the racks and (ii) configured to directly read the ID number of the wireless ID tag of each box in at least one rack without relying on any reader electronics of any rack. In this way, the storage system can be implemented without having to provide rack electronics. In other embodiments, each rack has rack electronics, and the storage system has at least one removable reader access device configured to be removably connected to the set of reader electronics of a rack in order to transmit the ID number of the wireless ID tag of each box in the rack outside of the outer container. In this way, the storage system can be implemented without having to provide reader electronics for every rack in the storage system.

In one embodiment, a storage system comprises a plurality of racks, an outer container configured to receive the plurality of racks, and reader electronics. Each rack is configured to receive a plurality of boxes, each box (i) having a wireless identification (ID) tag having an ID number and (ii) configured to receive one or more samples. The reader electronics are (i) external to and distinct from the racks and (ii) configured to directly read the ID number of the wireless ID tag of each box in at least one rack without relying on any reader electronics of any rack.

In certain embodiments of the foregoing, each rack has no reader electronics.

In certain embodiments of the foregoing, at least one rack has a wireless ID tag, and the reader electronics is configured to read the rack's wireless ID tag.

In certain embodiments of the foregoing, at least one rack has a sequence of one or more holes that represent an ID number for the rack, wherein the sequence is unique for the storage system, and the reader electronics is configured to detect the sequence of one or more holes.

In certain embodiments of the foregoing, at least one rack has a sequence of one or more holes that represent a rack configuration for the rack, and the reader electronics is configured to detect the sequence of one or more holes.

In certain embodiments of the foregoing, the storage system is a cold storage system, and the outer container is either a freezer or a dewar.

In certain embodiments of the foregoing, the outer container comprises a plurality of horizontal receptacles, each receptacle is configured to receive a rack in a horizontal direction, and each receptacle has a wall configured with a set of reader electronics configured to directly read the ID number of the wireless ID tag of each box in the rack in the receptacle without relying on any reader electronics of the rack.

In certain embodiments of the foregoing, the outer container comprises a single receptacle, the receptacle is configured to receive the plurality of racks, and a set of reader electronics is configured to directly read the ID number of the wireless ID tag of each box in at least one rack in the receptacle without relying on any reader electronics of the at least one rack.

In certain embodiments of the foregoing, the set of reader electronics is a handheld wand reader configured to be held adjacent to a rack in order to read the ID number of the wireless ID tag of each box in the rack.

In certain embodiments of the foregoing, the storage system comprises a plurality of sets of reader electronics, each set configured to be mounted to an exterior surface of a different rack in order to read the ID number of the wireless ID tag of each box in the corresponding rack.

In certain embodiments of the foregoing, the outer container is a dewar having an offset opening at the top of the dewar, and the dewar comprises a rotatable structure configured to receive the racks through the offset opening and selectively provide access to the racks stored in the dewar by rotating the rotatable structure.

In certain embodiments of the foregoing, the reader electronics are configured to transmit the ID number of each read wireless ID tag outside of the container.

In another embodiment, a storage system comprises a plurality of racks, an outer container configured to receive the plurality of racks, and at least one removable reader access device. Each rack (i) has a set of rack reader electronics and (ii) is configured to receive a plurality of boxes, each box (i) having a wireless ID tag having an ID number and (ii) configured to receive one or more samples, wherein each set of rack reader electronics is configured to read the ID number of the wireless ID tag of each box in at least one rack. The removable reader access device is configured to be removably connected to the set of rack reader electronics of a rack in order to transmit the ID number of the wireless ID tag of each box in the rack outside of the outer container.

In certain embodiments of the foregoing, the removable reader access device is a handheld device.

In certain embodiments of the foregoing, the storage system comprises a plurality of removable reader access devices, and each removable reader access device is configured to be removably connected to the set of rack reader electronics of a different rack.

In certain embodiments of the foregoing, the storage system is a cold storage system, and the outer container is either a freezer or a dewar.

In certain embodiments of the foregoing, the outer container comprises a plurality of horizontal receptacles, and each receptacle is configured to receive a rack in a horizontal direction.

In certain embodiments of the foregoing, the outer container comprises a single vertical receptacle, and the receptacle is configured to receive the plurality of racks in a vertical direction.

In certain embodiments of the foregoing, the outer container is a dewar having an offset opening at the top of the dewar, and the dewar comprises a rotatable structure configured to receive the racks through the offset opening and selectively provide access to the racks stored in the dewar by rotating the rotatable structure.

Embodiments of the invention may be implemented as (analog, digital, or a hybrid of both analog and digital) circuit-based processes, including possible implementation as a single integrated circuit (such as an ASIC or an FPGA), a multi-chip module, a single card, or a multi-card circuit pack. As would be apparent to one skilled in the art, various functions of circuit elements may also be implemented as processing blocks in a software program. Such software may be employed in, for example, a digital signal processor, micro-controller, general-purpose computer, or other processor.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, micro-code, and the like), an entirely hardware embodiment, or an embodiment combining software and hardware aspects that may generally be referred to herein as a "system."

Embodiments of the invention can be manifest in the form of methods and apparatuses for practicing those methods. Embodiments of the invention can also be manifest in the form of program code embodied in tangible media, such as magnetic recording media, optical recording media, solid state memory, floppy diskettes, CD-ROMs, hard drives, or any other non-transitory machine-readable storage medium, wherein, when the program code is loaded into and executed by a machine, such as a computer, the machine becomes an apparatus for practicing the invention. Embodiments of the invention can also be manifest in the form of program code, for example, stored in a non-transitory machine-readable storage medium including being loaded into and/or executed by a machine, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits.

Any suitable processor-usable/readable or computer-usable/readable storage medium may be utilized. The storage medium may be (without limitation) an electronic, magnetic, optical, electromagnetic, infrared, or semiconductor system, apparatus, or device. A more-specific, non-exhaustive list of possible storage media include a magnetic tape, a portable computer diskette, a hard disk, a random access memory (RAM), a read-only memory (ROM), an erasable programmable read-only memory (EPROM) or Flash memory, a portable compact disc read-only memory (CD-ROM), an optical storage device, and a magnetic storage device. Note that the storage medium could even be paper or another suitable medium upon which the program is printed, since the program can be electronically captured via, for instance, optical scanning of the printing, then compiled, interpreted, or otherwise processed in a suitable manner including but not limited to optical character recognition, if necessary, and then stored in a processor or computer memory. In the context of this disclosure, a suitable storage medium may be any medium that can contain or store a program for use by or in connection with an instruction execution system, apparatus, or device.

The functions of the various elements shown in the figures, including any functional blocks labeled as "processors," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

All documents mentioned herein are hereby incorporated by reference in their entirety or alternatively to provide the disclosure for which they were specifically relied upon.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

It should be appreciated by those of ordinary skill in the art that any block diagrams herein represent conceptual views of illustrative circuitry embodying the principles of the disclosure. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

Unless otherwise specified herein, the use of the ordinal adjectives "first," "second," "third," etc., to refer to an object of a plurality of like objects merely indicates that different instances of such like objects are being referred to, and is not intended to imply that the like objects so referred-to have to be in a corresponding order or sequence, either temporally, spatially, in ranking, or in any other manner.

What is claimed is:

1. A storage system comprising:

a plurality of sample receptacles, each sample receptacle (i) being a box, a blood bag, or a wax tissue block having a wireless identification (ID) tag having an ID number and (ii) each sample receptacle having an interior configured to receive one or more samples;

a plurality of racks, each rack having a plurality of locations, each location configured to receive one of the sample receptacles;

an outer container having an interior configured to receive the plurality of racks, wherein the outer container is a dewar; and reader electronics (i) external to and distinct from the racks and (ii) comprising a plurality of RFID reader antennae located inside the outer container and a system controller located outside the outer container and configured to communicate with the plurality of RFID reader antennae, wherein each of the RFID reader antennae is located sufficiently close to the wireless ID tag of a corresponding one of the sample receptacles in a corresponding rack to enable the RFID reader antenna to directly read the ID number of the wireless ID tag in order to send the read ID number to the system controller.

2. The storage system of claim 1, wherein:

at least one rack has a wireless ID tag; and the reader electronics reads the rack's wireless ID tag.

3. The storage system of claim 1, wherein:

at least one rack has a sequence of two or more holes that represent an ID number for the rack, wherein the sequence is unique for the storage system; and the reader electronics detects the sequence of two or more holes.

4. The storage system of claim 1, wherein:

at least one rack has a sequence of two or more holes that represent a rack configuration for the rack; and the reader electronics detects the sequence of two or more holes.

5. The storage system of claim 1, wherein the reader electronics comprises a wand reader configured to communicate with the system controller and holdable adjacent to a rack in order to receive, from a corresponding RFID reader antenna of the plurality of RFID reader antennae, the ID number of the wireless ID tag of each sample receptacle in the rack.

6. The storage system of claim 1, wherein the reader electronics comprises a plurality of wand readers, each wand reader configured to communicate with the system controller and mountable adjacent to a corresponding rack in order to receive, from a corresponding RFID reader antenna of the plurality of RFID reader antennae, the ID number of the wireless ID tag of each sample receptacle in the corresponding rack.

7. The storage system of claim 1, wherein:

the dewar has an offset opening at the top of the dewar; and the dewar comprises a rotatable structure receiving the racks through the offset opening and selectively providing access to the racks stored in the dewar by rotating the rotatable structure, wherein the offset opening is offset relative to a spindle of the rotatable structure.

8. The storage system of claim 1, wherein the reader electronics comprises a relay circuit located inside the outer container and configured to receive from a corresponding RFID reader antenna of the plurality of RFID reader antennae, the ID number of a corresponding read wireless ID tag and transmit the ID number of the corresponding read wireless ID tag to the system controller located outside of the outer container.

9. A storage system comprising:

a plurality of sample receptacles, each sample receptacle (i) being a box, a blood bag, or a wax tissue block having a wireless ID tag having an ID number and (ii) having an interior configured to receive one or more samples;

a plurality of racks, each rack (i) having a set of rack reader electronics and (ii) having locations, each location configured to receive one or more of the sample receptacles, wherein each set of rack reader electronics comprises one or more RFID reader antennae and RFID reader circuitry electrically connected to the one or more RFID reader antennae, wherein the set of rack reader electronics is configured to read the ID number of the wireless ID tag of each sample receptacle in at least one rack;

an outer container having an interior configured to receive the plurality of racks; and at least one removable reader access device comprising (i) a read head removably electrically connected to the set of rack reader electronics of a rack and configured to receive the ID number of the wireless ID tag of each sample receptacle in the rack and (ii) a display connected to receive the ID number of the wireless ID tag of each sample receptacle in the rack from the read head via a wired or wireless connection and configured to display the ID number of the wireless ID tag of each sample receptacle in the rack with the read head located inside the outer container and the display located either inside or outside of the outer container.

10. The storage system of claim 9, wherein the removable reader access device is a handheld device.

11. The storage system of claim 9, wherein:

the removable reader access device is part of a plurality of removable reader access devices of the storage system; and the plurality of removable reader access devices are removably connectable to the sets of rack reader electronics of different ones of the plurality of racks.

12. The storage system of claim 9, wherein the outer container is either a freezer or a dewar.

13. The storage system of claim 9, wherein:

the outer container comprises a plurality of vertical rack receptacles; and each vertical rack receptacle having a compartment configured to receive a rack of the plurality of racks in a vertical direction.

14. The storage system of claim 9, wherein:

the outer container comprises a single vertical rack receptacle; and the vertical rack receptacle having a compartment configured to receive the plurality of racks in a vertical direction.

15. The storage system of claim 14, wherein:

the outer container is a dewar having an offset opening at the top of the dewar; and the dewar comprises a rotatable structure receiving the racks through the offset opening and selectively providing access to the racks stored in the dewar by rotating the rotatable structure, wherein the offset opening is offset relative to a spindle of the rotatable structure.

16. A storage system comprising:

a plurality of sample receptacles, each sample receptacle (i) being a box, a blood bag, or a wax tissue block having a wireless identification (ID) tag having an ID number and (ii) each sample receptacle having an interior configured to receive one or more samples;

a plurality of racks, each rack having a plurality of locations, each location configured to receive one of the sample receptacles;

an outer container having an interior configured to receive the plurality of racks; and reader electronics (i) external to and distinct from the racks and (ii) comprising a plurality of RFID reader antennae located inside the outer container and a system controller located outside the outer container and configured to communicate with the plurality of RFID reader antennae, wherein each of the RFID reader antennae is located sufficiently close to the wireless ID tag of a corresponding one of the sample receptacles in a corresponding rack to enable the RFID reader antenna to directly read the ID number of the wireless ID tag in order to send the read ID number to the system controller, wherein the reader electronics comprises a relay circuit located inside the outer container and configured to receive, from a corresponding RFID reader antenna of the plurality of RFID reader antennae, the ID number of a corresponding read wireless ID tag and transmit the ID number of the corresponding read wireless ID tag to the system controller located outside of the outer container.

* * * * *